United States Patent
Wood

(10) Patent No.: US 11,369,289 B2
(45) Date of Patent: Jun. 28, 2022

(54) SYSTEM AND METHOD FOR AUTOMATICALLY MONITORING PHYSIOLOGICAL PARAMETERS OF A SUBJECT

(71) Applicant: Inspired Performance Institute, Inc., Windermere, FL (US)

(72) Inventor: Donald A. Wood, Windermere, FL (US)

(73) Assignee: Inspired Performance Institute, Inc., Windermere, FL (US)

( * ) Notice: Subject to any disclaimer, the term of this patent is extended or adjusted under 35 U.S.C. 154(b) by 668 days.

(21) Appl. No.: 16/180,440

(22) Filed: Nov. 5, 2018

(65) Prior Publication Data

US 2019/0133496 A1 May 9, 2019

Related U.S. Application Data

(60) Provisional application No. 62/581,349, filed on Nov. 3, 2017.

(51) Int. Cl.
*A61B 5/11* (2006.01)
*A61B 5/0205* (2006.01)
*A61B 5/00* (2006.01)
*A61B 5/01* (2006.01)
*A61B 5/024* (2006.01)

(52) U.S. Cl.
CPC .......... *A61B 5/1118* (2013.01); *A61B 5/0002* (2013.01); *A61B 5/01* (2013.01); *A61B 5/02055* (2013.01); *A61B 5/486* (2013.01); *A61B 5/4836* (2013.01); *A61B 5/681* (2013.01); *A61B 5/7207* (2013.01); *A61B 5/7289* (2013.01); *A61B 5/7455* (2013.01); *A61B 5/02416* (2013.01);
(Continued)

(58) Field of Classification Search
CPC ....... A61B 5/1118; A61B 5/0002; A61B 5/01; A61B 5/02055; A61B 5/4836; A61B 5/486; A61B 5/681; A61B 5/7207; A61B 5/7289; A61B 5/7455; A61B 5/02416; A61B 5/02438; A61B 2560/0214
See application file for complete search history.

(56) References Cited

U.S. PATENT DOCUMENTS 4,305,401 A 12/1981 Reissmeuller
4,312,358 A 1/1982 Barney
(Continued)

*Primary Examiner* — Tammie K Marlen
(74) *Attorney, Agent, or Firm* — Timothy H. Van Dyke; Wolter, Van Dyke, Davis, PLLC

(57) ABSTRACT

A method and assembly for monitoring physiological parameters of a subject is provided. The method includes measuring, with a physiological sensor, data that indicates a change in a value of a physiological parameter of a subject over a time period. The method further includes measuring, with a motion sensor, data that indicates a value of a motion of the subject over the time period. The method further includes determining, with a processor, whether the value of the motion of the subject over the time period is less than a motion threshold. The method includes determining, with the processor, whether the change in the value of the physiological parameter over the time period exceeds a change threshold. The method also includes performing an action based on the determination that the change in the value of the physiological parameter exceeds the change threshold.

20 Claims, 9 Drawing Sheets

(52) U.S. Cl.
CPC ... *A61B 5/02438* (2013.01); *A61B 2560/0214* (2013.01)

(56) References Cited

U.S. PATENT DOCUMENTS

| | | |
|---|---|---|
| 7,993,276 B2 | 8/2011 | Nazarian et al. |
| 8,446,275 B2 | 5/2013 | Utter, II |
| 9,318,013 B2 | 4/2016 | Zohar |
| 9,460,262 B2 | 10/2016 | Kaufman et al. |
| 2003/0139654 A1 | 7/2003 | Kim et al. |
| 2011/0245633 A1 | 10/2011 | Goldberg et al. |
| 2011/0257553 A1* | 10/2011 | Banet ............... A61B 5/0816 600/536 |
| 2013/0072765 A1 | 9/2013 | Kinsolving |
| 2014/0221854 A1 | 8/2014 | Wai |
| 2015/0313542 A1 | 11/2015 | Goldberg et al. |
| 2015/0374310 A1* | 12/2015 | Lee ................. A61B 5/7285 600/483 |
| 2016/0029964 A1* | 2/2016 | LeBoeuf ........... A61B 5/6815 600/476 |
| 2016/0035206 A1* | 2/2016 | Pai .................. A61B 5/1117 340/539.12 |
| 2017/0209055 A1* | 7/2017 | Pantelopoulos ..... A61B 5/7203 |

* cited by examiner

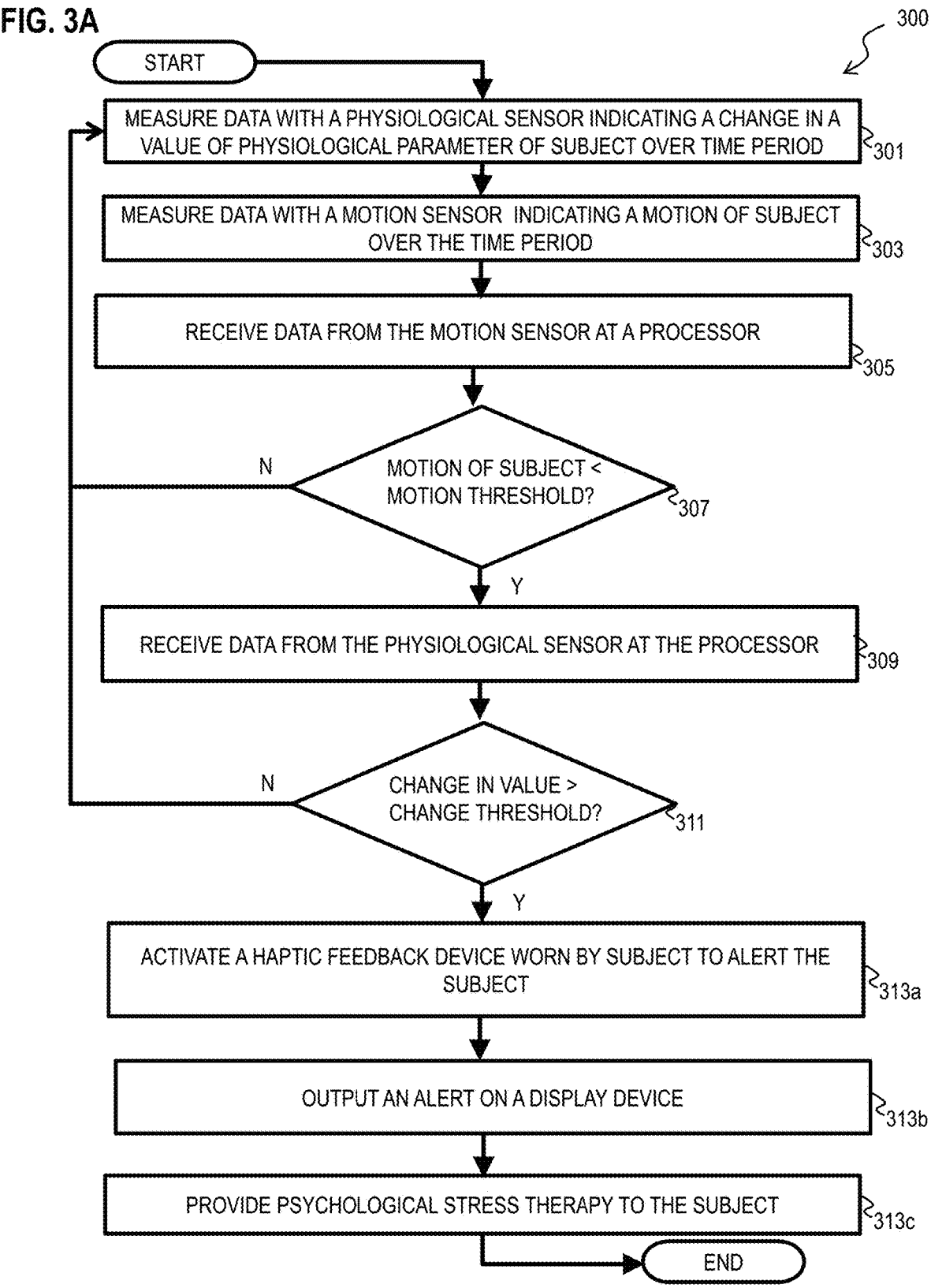

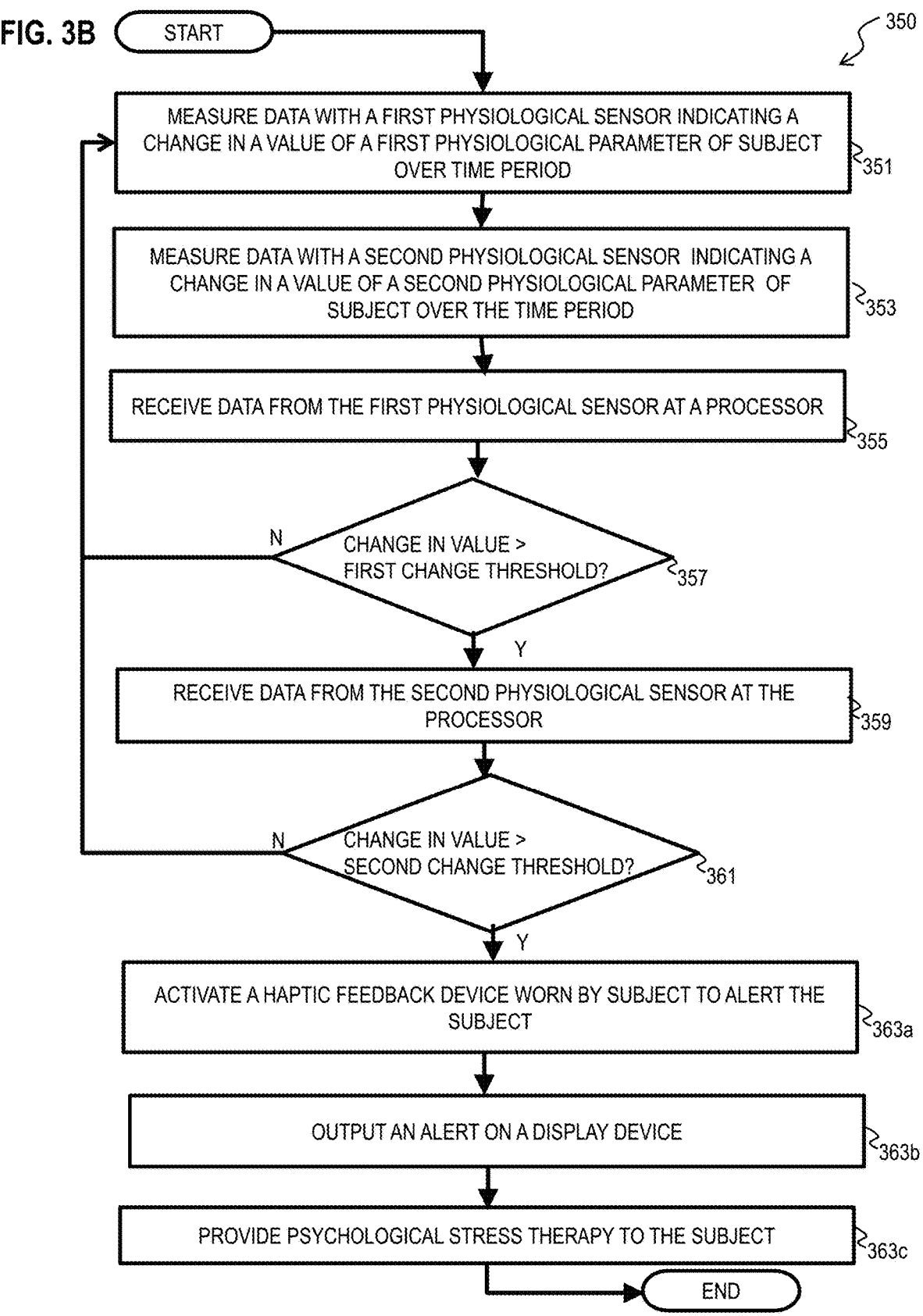

FIG. 8    Table

| Client | EX1 Pre | EX1 Post | SK1 Pre | SK2 Post | TE1 Pre | TE1 Post | MI1 Pre | MI2 Post | MF1 Pre | MF2 Post | MM1 Pre | MM2 Post | MD1 Pre | MD2 Post |
|---|---|---|---|---|---|---|---|---|---|---|---|---|---|---|
| Item | | | | | | | | | | | | | | |
| Emotional Stability | 7 | 5 | 3 | 4 | 5 | 6 | 5 | 5 | 4 | 2 | 5 | 5 | 5 |
| Mental Clarity | 5 | 5 | 8 | 6 | 4 | 5 | 6 | 6 | 5 | 5 | 5 | 5 | 5 |
| Vagal Tone | 1 | 5 | 2 | 5 | 3 | 5 | 5 | 5 | 3 | 7 | 5 | 5 |
| HDL-C | 2 | 4 | 7 | 6 | 5 | 5 | 2 | 6 | 5 | 3 | 4 | 3 | 5 |
| LDL-C Direct * | 5 | 5 | 6 | 5 | 4 | 5 | 2 | 3 | 5 | 7 | 5 | 7 | 4 |
| Neutral Fat | 6 | 5 | 7 | 5 | 4 | 5 | 8 | 5 | 5 | 9 | 6 | 8 | 4 |
| Non HDL C * | 5 | 5 | 8 | 6 | 6 | 4 | 5 | 5 | 5 | 5 | 5 | 5 | 5 |
| Total Cholesterol | 7 | 6 | 2 | 5 | 6 | 5 | 5 | 6 | 6 | 3 | 6 | 5 | 4 |
| Triglycerides | 3 | 5 | 6 | 6 | 6 | 6 | 5 | 5 | 5 | 6 | 5 | 5 | 5 |
| Albumin | 2 | 5 | 7 | 4 | 5 | 4 | 5 | 5 | 5 | 5 | 5 | 3 | 2 | 5 |
| Circulating Immune Complex * | 5 | 6 | 8 | 5 | 5 | 5 | 5 | 5 | 6 | 5 | 5 | 5 | 6 | 5 |
| Ferritin | 5 | 4 | 4 | 5 | 6 | 8 | 5 | 5 | 4 | 5 | 4 | 5 | 5 |
| Rheumatism | 5 | 5 | 4 | 5 | 2 | 5 | 5 | 4 | 5 | 5 | 5 | 5 | 3 | 5 |
| Cranial Nerve 10, Vagus Nerve * | 3 | 4 | 6 | 5 | 5 | 5 | 5 | 5 | 6 | 5 | 6 | 6 | 5 | 6 |
| Parasympathetic NS Function * | 5 | 5 | 5 | 5 | 5 | 2 | 5 | 8 | 5 | 8 | 8 | 5 | 6 | 4 |
| Sympathetic NS Function * | 5 | 5 | 5 | 6 | 4 | 6 | 6 | 8 | 6 | 8 | 5 | 5 | 5 | 5 |
| Adrenal Cortex * | 5 | 6 | 6 | 5 | 5 | 2 | 5 | 7 | 5 | 5 | 5 | 3 | 5 | 5 |
| Thyroid * | 5 | 5 | 5 | 5 | 5 | 9 | 6 | 5 | 5 | 4 | 5 | 5 | 5 | 8 |
| Gastric Absorption | 4 | 5 | 5 | 1 | 4 | 6 | 4 | 6 | 5 | 5 | 5 | 3 | 4 | 5 |
| Cortisol * | 5 | 6 | 5 | 5 | 5 | 3 | 4 | 4 | 5 | 3 | 5 | 5 | 5 | 5 |
| GABA * | 5 | 5 | 5 | 5 | 5 | 3 | 5 | 1 | 5 | 7 | 5 | 6 | 5 | 6 |
| Serotonin * | 8 | 7 | 5 | 5 | 5 | 2 | 5 | 5 | 5 | 7 | 5 | 5 | 5 | 4 |
| Cortisol Dysfunction * | 5 | 5 | 5 | 2 | 5 | 6 | 5 | 4 | 4 | 6 | 5 | 5 | 6 | 5 |
| Cytokine Activity | 2 | 4 | 4 | 8 | 5 | 6 | 6 | 1 | 4 | 3 | 5 | 6 | 6 | 6 |
| Fibrinogen | 5 | 6 | 6 | 4 | 5 | 5 | 6 | 5 | 3 | 5 | 5 | 7 | 5 | 4 |
| HS-CRP | 3 | 3 | 4 | 5 | 5 | 7 | 6 | 9 | 6 | 5 | 6 | 6 | 4 | 5 |
| Homocysteine | 3 | 3 | 4 | 7 | 5 | 6 | 6 | 2 | 3 | 6 | 5 | 5 | 5 | 4 |
| Histamine | 5 | 5 | 4 | 4 | 5 | 5 | 5 | 8 | 5 | 5 | 5 | 5 | 5 | 4 |
| Lp-PLA2 | 5 | 5 | 4 | 5 | 5 | 5 | 4 | 2 | 5 | 8 | 5 | 9 | 8 | 5 |
| Myeloperoxidase | 6 | 7 | 5 | 5 | 5 | 5 | 4 | 4 | 4 | 4 | 5 | 5 | 5 | 4 |
| nf-Kappa b | 2 | 5 | 6 | 6 | 6 | 5 | 5 | 6 | 6 | 5 | 5 | 5 | 5 | 5 |
| Sedimentation Rate | 2 | 2 | 5 | 8 | 6 | 3 | 4 | 5 | 4 | 2 | 5 | 5 | 5 | 5 |
| Leptin | 6 | 5 | 6 | 7 | 5 | 7 | 8 | 6 | 5 | 5 | 4 | 3 | 4 |
| Bile Secretion Function | 1 | 2 | 7 | 6 | 7 | 5 | 6 | 4 | 5 | 4 | 5 | 5 |

SYSTEM AND METHOD FOR AUTOMATICALLY MONITORING PHYSIOLOGICAL PARAMETERS OF A SUBJECT

BACKGROUND

Physiological sensors such as heart rate sensors and temperature sensors have been used in conventional systems to measure a value of physiological parameters of a subject, such as heart rate and body temperature. In these conventional systems, the measured values of the heart rate and body temperature are monitored to predict a health condition of the subject.

SUMMARY

Techniques are provided for automatically monitoring physiological parameters of a subject. The current inventor recognized that conventional systems that are used for monitoring physiological parameters of a subject have notable drawbacks. In one example, conventional systems monitor the physiological parameter values (e.g. heart rate, temperature) of the subject and predict a health condition based on whether the physiological parameter values exceed a threshold value. However, the current inventor recognized that conventional systems are not capable of ruling out alternative reasons other than an adverse health condition (e.g. subject is exercising) for elevated physiological parameter values. Thus, these conventional systems are prone to generate false positive alerts that the subject is experiencing an adverse health condition (e.g. heart attack, panic attack). A system and method is provided that addresses this drawback of conventional systems for monitoring physiological parameters of a subject.

Techniques are also provided for treating one or more adverse health conditions (e.g. heart attack, panic attack, etc) that is determined by a method for monitoring physiological parameters of the subject. Additionally, methods for assessing the effectiveness of such techniques of treating these adverse health conditions are also provided.

In a first set of embodiments, an assembly is provided for monitoring physiological parameters based on motion of a subject. The assembly includes a physiological sensor to measure data that indicates a change in a value of a physiological parameter of the subject over a time period. The assembly also includes a motion sensor to measure data that indicates a value of a motion of the subject over the time period. The assembly also includes a processor and a memory including one or more sequences of instructions. The memory and sequences of instructions cause the assembly to receive data from the motion sensor and determine whether the value of the motion of the subject over the time period is less than a motion threshold. The memory and sequences of instructions further cause the assembly to receive data from the physiological sensor over the time period if the value of the motion of the subject is less than the motion threshold. The memory and sequences of instructions further cause the assembly to determine whether the change in the value of the physiological parameter over the time period exceeds a change threshold. The memory and sequences of instructions further cause the assembly to perform an action based on the determination that the change in the value of the physiological parameter exceeds the change threshold.

In a second set of embodiments, an assembly is provided for monitoring physiological parameters of a subject. The assembly includes a first physiological sensor to measure data that indicates a change in a value of a first physiological parameter of the subject over a time period. The assembly also includes a second physiological sensor to measure data that indicates a change in a value of a second physiological parameter of the subject over the time period. The assembly also includes a processor and a memory including one or more sequences of instructions. The memory and sequences of instructions cause the assembly to receive data from the first physiological sensor over the time period and determine whether the change in the value of the first physiological parameter exceeds a first change threshold. The memory and sequences of instructions further cause the assembly to receive data from the second physiological sensor over the time period if the change in the value of the first physiological parameter exceeds the first change threshold. The memory and sequences of instructions further cause the assembly to determine whether the change in the value of the second physiological parameter exceeds a second change threshold. The memory and sequences of instructions further cause the assembly to perform an action based on the determination that the change in the value of the second physiological parameter exceeds the second change threshold.

In a third set of embodiments, a method is provided for monitoring physiological parameters based on movement of a subject. The method includes measuring, with a physiological sensor, data that indicates a change in a value of a physiological parameter of the subject over a time period. The method also includes measuring, with a motion sensor, data that indicates a value of a motion of the subject over the time period. The method also includes receiving, with a processor, data from the motion sensor and determining whether the value of the motion of the subject over the time period is less than a motion threshold. The method also includes receiving, with the processor, data from the physiological sensor if the value of the motion of the subject is less than the motion threshold. The method also includes determining, with the processor, whether the change in the value of the physiological parameter over the time period exceeds a change threshold. The method also includes performing an action based on the determination that the change in the value of the physiological parameter exceeds the change threshold.

In a fourth set of embodiments, a method is provided for monitoring physiological parameters of a subject. The method includes measuring, with a first physiological sensor, data that indicates a change in a value of a first physiological parameter of the subject over a time period. The method also includes measuring, with a second physiological sensor, data that indicates a change in a value of a second physiological parameter of the subject over the time period. The method also includes receiving, with a processor, data from the first physiological sensor over the time period and determining whether the change in the value of the first physiological parameter exceeds a first change threshold. The method also includes receiving, with the processor, data from the second physiological sensor over the time period if the change in the value of the first physiological parameter exceeds the first change threshold. The method also includes determining, with the processor, whether the change in the value of the second physiological parameter exceeds a second change threshold. The method also includes performing an action based on the determination that the change in the value of the second physiological parameter exceeds the second change threshold.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 3A is a flow chart that illustrates an example method for automatically monitoring a physiological parameter based on motion of a subject, according to an embodiment;

FIG. 3B is a flow chart that illustrates an example method for automatically monitoring a physiological parameter of a subject, according to an embodiment;

FIG. 8 is a table that illustrates example parameter data of subjects taken before and after the treatment of the method, according to an embodiment.

DETAILED DESCRIPTION

Figure 1:
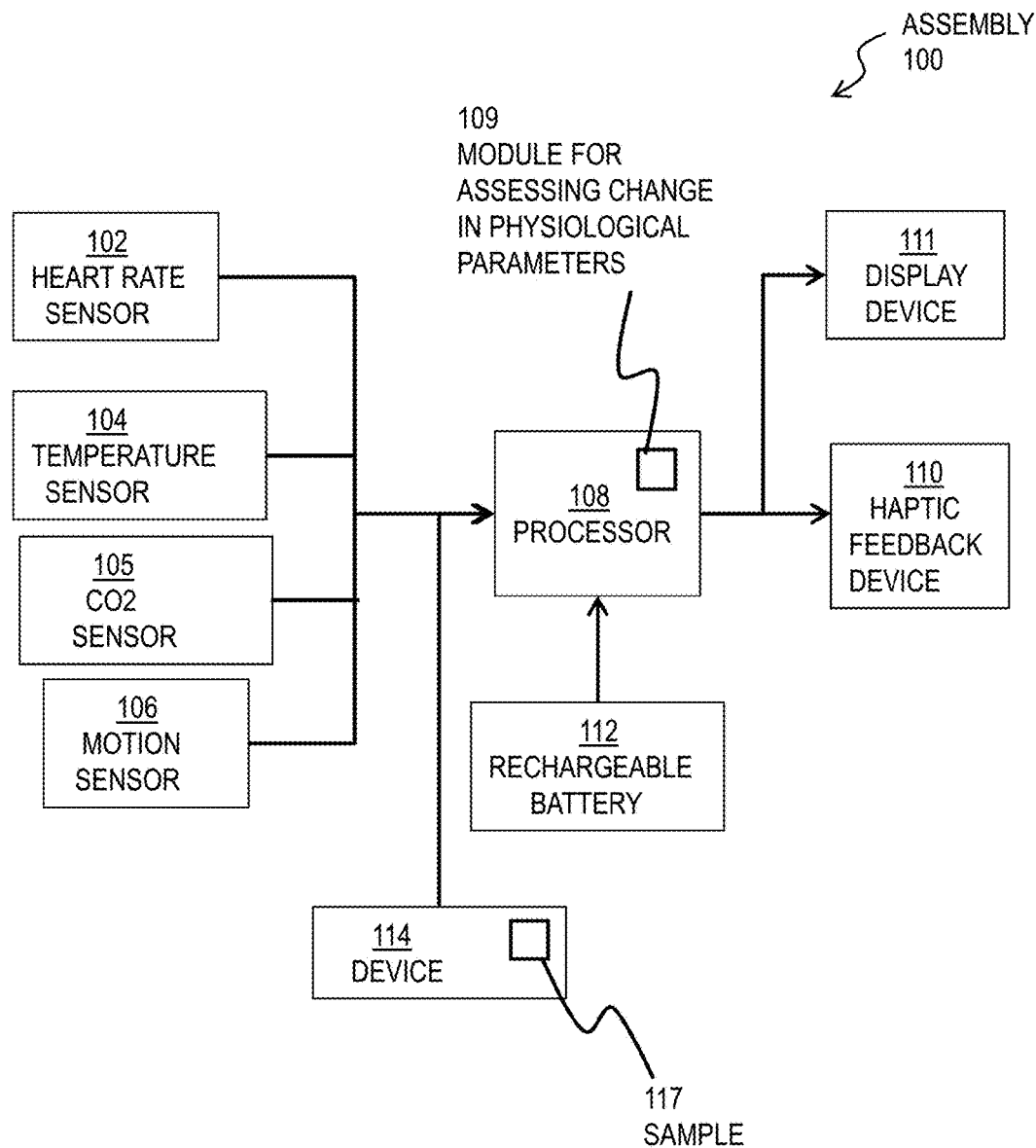
FIG. 1 is a block diagram that illustrates example components of an assembly for automatically monitoring a physiological parameter of a subject, according to an embodiment.

A method and assembly are described for automatically monitoring physiological parameters of a subject. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of monitoring a physiological parameter of a subject. In one example embodiment, the invention is described in the context of monitoring a physiological parameter of a subject based on a level of physical activity of the subject. In another example embodiment, the invention is described in the context of monitoring a change in a value of a first physiological parameter of a subject based on a change in a value of a second physiological parameter of the subject. In one example embodiment, the invention is described in the context of predicting an onset of an adverse health condition of the subject. In another example embodiment, the invention is described in the context of predicting an onset of a panic attack of the subject. However, the invention is not limited to this context. In other embodiments, the invention is described in the context of predicting an onset of health conditions including one or more of a heart attack, an anxiety episode or Post-Traumatic Stress Disorder (PTSD) flashbacks. In still other embodiments, the invention is described in the context of treatments that are provided based on determination of an onset of a health condition. In still other embodiments, the invention is described in the context of a method for assessing the effectiveness of treatments that are provided after determining the onset of the health conditions.

1. Overview

FIG. 1 is a block diagram that illustrates example components of an assembly 100 for automatically monitoring a physiological parameter of a subject, according to an embodiment. The assembly 100 includes one or more physiological sensors to measure data that indicates a change in a value of a physiological parameter of a subject over a time period.

In one embodiment, the physiological sensor is a heart rate sensor 102 to measure data that indicates a change in a heart rate of the subject over the time period. In one embodiment, the heart rate sensor 102 is an optical heart-rate monitor that measures the data through photoplethysmography (PPG), or a process of using light to measure blood flow. In an example embodiment, a wrist band incorporates the heart rate sensor 102 and includes small light emitting diodes (LEDs) on an underside of the sensor 102 that shines green light onto the skin of the wrist of the subject. The different wavelengths of light from these optical emitters interact differently with the blood flowing through the wrist of the subject. When that light refracts (or reflects) off the flowing blood of the subject, the heart rate sensor 102 captures that information. This data is processed to generate the data that indicates the heart rate of the subject and the change in the heart rate of the subject over the time period. In another embodiment, the heart rate sensor 102 includes a transmitter that is strapped to a body of the subject (e.g. chest) and a receiver (e.g. in a wrist band or smart phone). The transmitter includes electrodes placed against the skin that use electrocardiography to record electrical activity of the heart (e.g. EKG signal) of the subject. A processor analyzes the EKG signal to determine the heart rate of the subject and/or the change in the heart rate over the time period.

In another embodiment, the physiological sensor is a temperature sensor 104 to measure a change in a body temperature of the subject over the time period. In one example embodiment, the temperature sensor 104 is an infrared thermopile sensor.

In some embodiments, the assembly 100 includes the heart rate sensor 102 and the temperature sensor 104. In other embodiments, the assembly 100 includes the heart rate sensor 102 and excludes the temperature sensor 104. In still other embodiments, the assembly 100 includes the temperature sensor 104 and excludes the heart rate sensor 102. Although FIG. 1 depicts the heart rate sensor 102 and temperature sensor 104, the physiological sensor of the assembly 100 is not limited to these sensors 102, 104 and includes any physiological sensor to measure any physiological parameter of the subject, such as breathing rate, sense of orientation and perspiration. In one embodiment, the physiological sensor is a CO2 (Carbon Dioxide) sensor 105 that detects a level of CO2 in the breath of the subject. In yet another embodiment, the physiological sensor is a pulse oximeter and the measured physiological parameter is oxygen saturation (SO2). In this embodiment, the CO2 sensor 105 measures data that indicates a level of CO2 in the breath of the subject. In an example embodiment, the assembly 100 includes the CO2 sensor 105 and the heart rate sensor 102 and/or the temperature sensor 104.

In some embodiments, the assembly 100 includes a motion sensor 106 to measure data that indicates a value of a motion of the subject over the time period. In one embodiment, the motion sensor 106 is excluded and the heart rate sensor 102 and temperature sensor 104 are included. In another embodiment, the temperature sensor 104 is excluded and the motion sensor 106 and heart rate sensor 102 are included.

In one embodiment, the motion sensor 106 is an accelerometer that measures data that indicates a value of an acceleration of the subject over the time period (e.g. linear and/or rotational acceleration). In an example embodiment, the accelerometer is a three-axis accelerometer. In another embodiment, the motion sensor 106 is a position sensor that measures data that indicates a value of a position of the subject over the time period. In an example embodiment, the position sensor is a Global Positioning System (GPS) sensor.

Figure 4:
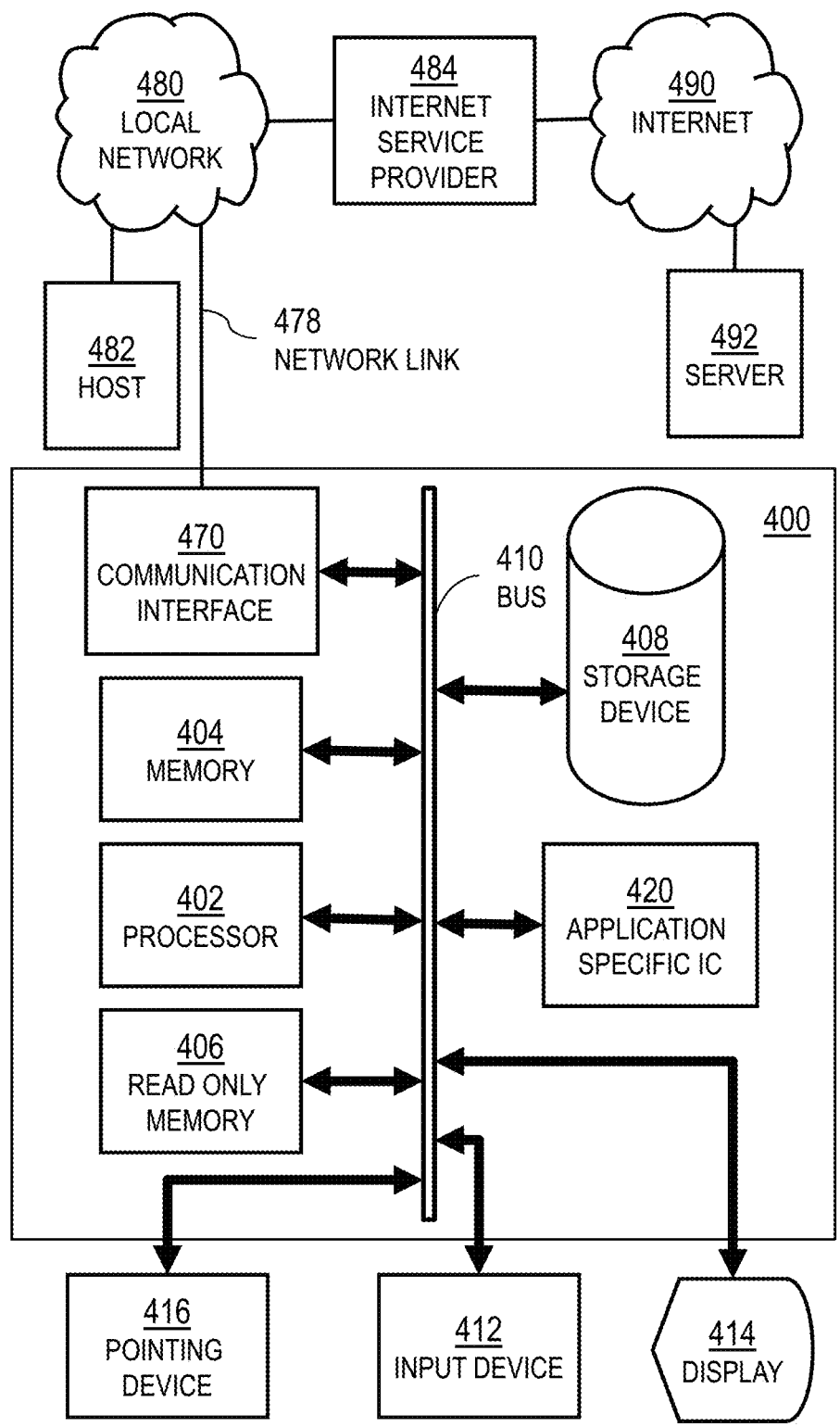
FIG. 4 is a block diagram that illustrates a computer system upon which an embodiment of the invention may be implemented.
Figure 5:
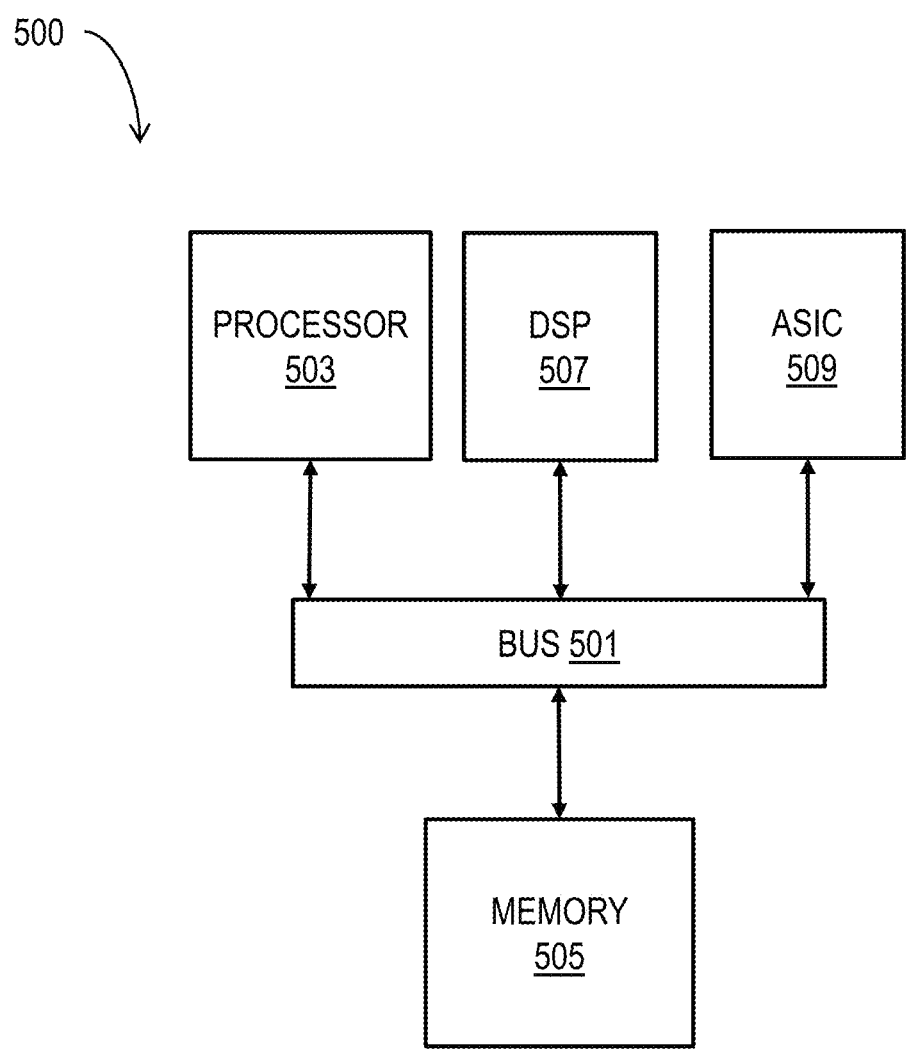
FIG. 5 illustrates a chip set upon which an embodiment of the invention may be implemented.
Figure 6:
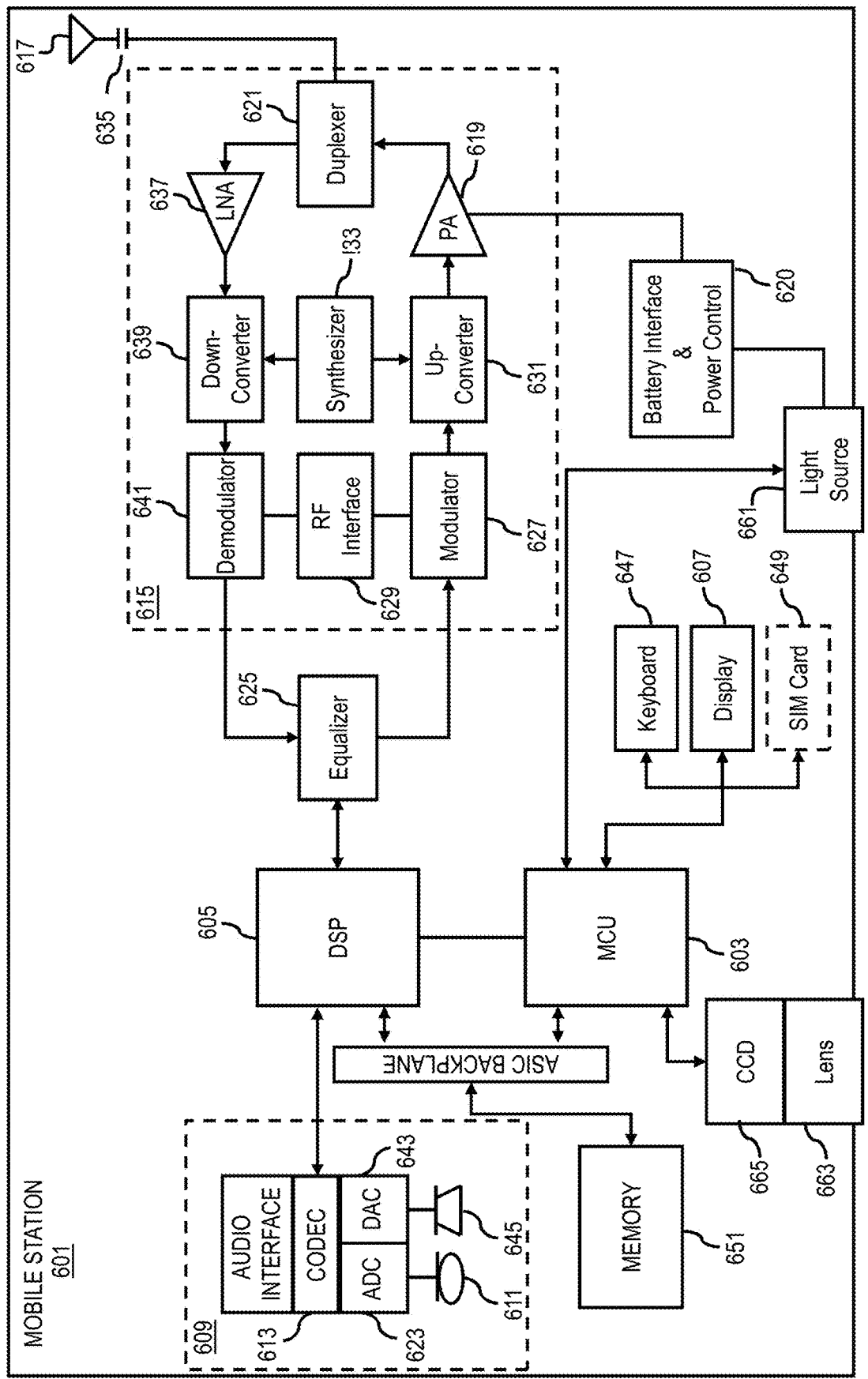
FIG. 6 illustrates a mobile terminal upon which an embodiment of the invention may be implemented.

The assembly 100 includes a processor 108 that receives data from one or more of the heart rate sensor 102, temperature sensor 104 and motion sensor 106 over the time period. In an example embodiment, the processor 108 receives data from the CO2 sensor 105 over the time period. The processor 108 includes a module 109 for assessing change in physiological parameters that performs one or more steps of a method described below with reference to FIG. 3A or one or more steps of a method described below with reference to FIG. 3B. In an example embodiment, where the physiological sensor is the CO2 sensor 105, the module 109 assesses change in the level of CO2 based on one or more steps of the method with reference to FIG. 3A or one or more steps with reference to FIG. 3B. In various embodiments, the processor 108 comprises one or more general computer systems, as depicted in FIG. 4 or one or more chip sets as depicted in FIG. 5 or one or more mobile terminals as depicted in FIG. 6, and instructions to cause the computer or chip set or mobile terminal to perform one or more steps of a method described below with reference to FIG. 3A or a method described below with reference to FIG. 3B.

In some embodiments, the assembly 100 includes a haptic feedback device 110 that generates mechanical stimulation (e.g. force, vibration, motion, etc.) that is detected by the subject. In an example embodiment, the haptic feedback device is a vibration transducer. In some embodiments, the haptic feedback device 110 is worn on a body of the subject (e.g. wrist band). In other embodiments, the haptic feedback device 110 is integral with one or more of the heart rate sensor 102, temperature sensor 104, CO2 sensor 105, motion sensor 106 and processor 108 and worn on the body of the subject (e.g. wrist band). In one embodiment, the processor 108 activates the haptic feedback device 110 to generate mechanical stimulation detected by the subject, based on the assessment of the data from one or more of the heart rate sensor 102, temperature sensor 104, CO2 sensor 105 and motion sensor 106. In another embodiment, the device 110 is an audible device that outputs an auditory alert that is detected by the subject and is activated by the processor 108 based on the assessment of the data from one or more of the heart rate sensor 102, temperature sensor 104, CO2 sensor 105 and motion sensor 106.

In some embodiments, the assembly 100 includes a display device 111. In some embodiments, the display device 111 is on an article worn on the subject (e.g. wrist band). In other embodiments, the display device 111 is integrated with one or more of the heart rate sensor 102, temperature sensor 104, CO2 sensor 105, motion sensor 106 and processor 108 in the article worn on the body of the subject (e.g. wrist band). In some embodiments, the display device 111 is integrated in one of a chest strap, a ring, and a device that clips onto a finger or an ear of the subject. In one embodiment, the processor 108 causes one or more characters to be output on the display device 111, based on the assessment of the data from one or more of the heart rate sensor 102, temperature sensor 104, CO2 sensor 105 and motion sensor 106.

In some embodiments, the assembly 100 includes a rechargeable battery 112 that is used to power one or more of the processor 108, the heart rate sensor 102, the temperature sensor 104, the CO2 sensor 105 and the motion sensor 106. In one embodiment, the assembly 100 includes a plug (e.g. Micro B USB connector plug) to connect an external power source with the rechargeable battery 112 in order to recharge the battery 112. In other embodiments, an external power source (e.g. power outlet) is used to power the processor 108, heart rate sensor 102, the temperature sensor 104, the CO2 sensor 105 and the motion sensor 106 and thus need not include a battery.

Figure 2:
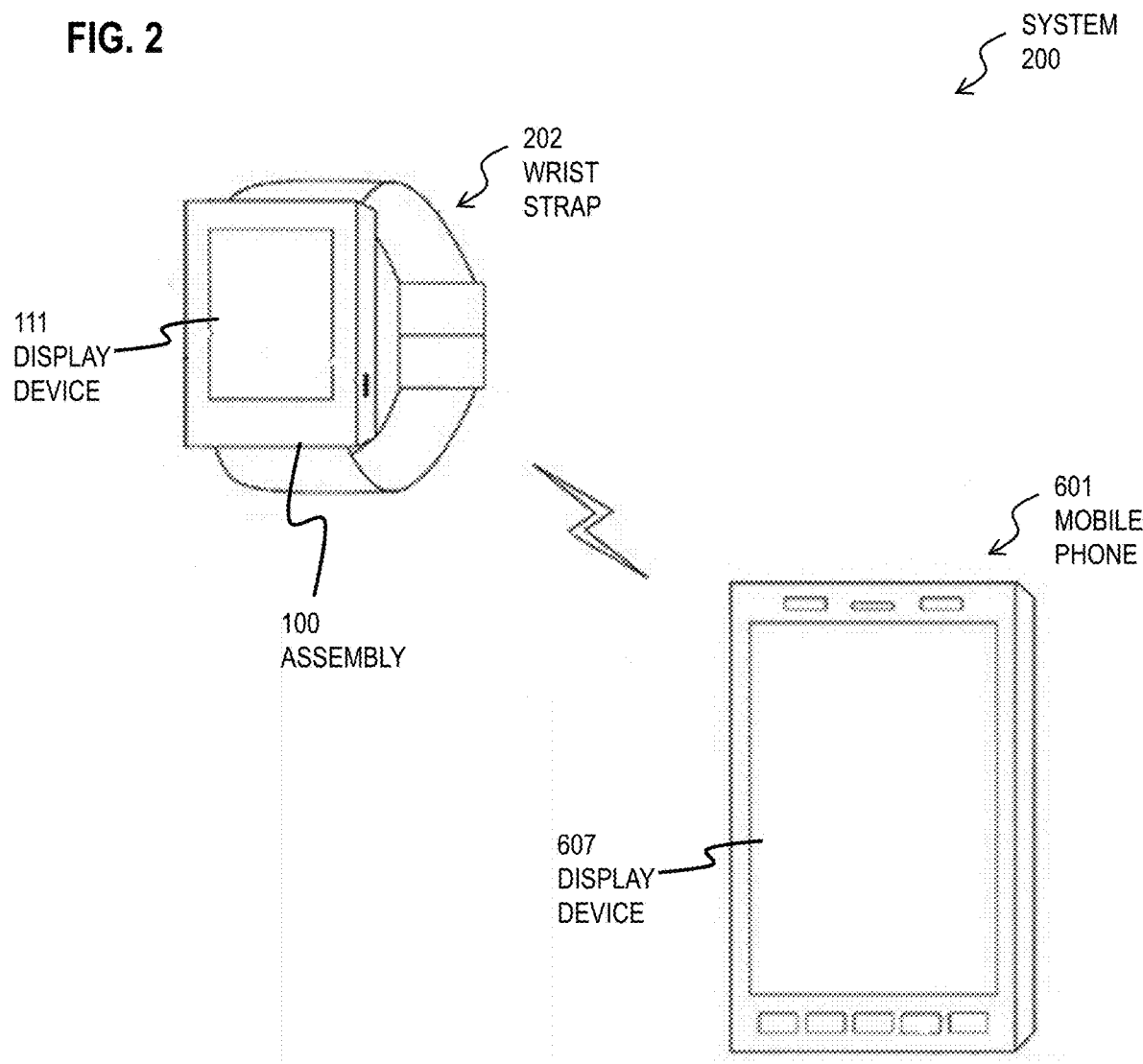
FIG. 2 is a block diagram that illustrates example components of a system for automatically monitoring a physiological parameter of a subject, according to an embodiment.

FIG. 2 is a block diagram that illustrates example components of a system 200 for automatically monitoring a physiological parameter of a subject, according to an embodiment. In an embodiment, the system 200 includes an article worn on the body of the subject, such as a wrist strap 202. The wrist strap 202 incorporates the assembly 100. In one embodiment, the assembly 100 includes the display device 111. In some embodiments, the system 200 includes a mobile phone 601 that is further depicted in FIG. 6 and includes a display device 607. In one embodiment, the system 200 excludes the display device 111 and the processor 108 causes one or more characters to be output on the display device 607 on the mobile phone 601 based on the assessment of data from one or more of the heart rate sensor 102, temperature sensor 104, CO2 sensor 105, and motion sensor 106. In an embodiment, the assembly 100 and the mobile phone 601 are in wireless communication (e.g. Bluetooth®). In an example embodiment, updates to the module 109 are communicated from the mobile phone 601 to the processor 108 of the assembly 100 using the wireless communication.

Although steps are depicted in FIG. 3A, and in subsequent flowchart FIG. 3B, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

FIG. 3A is a flow chart that illustrates an example method 300 for automatically monitoring a physiological parameter based on motion of a subject, according to an embodiment. In step 301, data is measured with a physiological sensor that indicates a change in a value of a physiological parameter of the subject over a time period. In one embodiment, the physiological sensor is the heart rate sensor 102 that measures data that indicates a change in a value of the heart rate of the subject over the time period. In another embodiment, the physiological sensor is the temperature sensor 104 that measures data that indicates a change in a value of the body temperature of the subject over the time period. In yet another embodiment, the physiological sensor is the CO2 sensor 105 that measures data that indicates a level of CO2 in the breath of the subject over the time period.

In step 303, data is measured by the motion sensor 106 that indicates a value of the motion of the subject over the time period. In one example embodiment, where the motion sensor 106 is an accelerometer, the sensor 106 measures an acceleration of the subject over the time period. In another example embodiment, where the motion sensor 106 is a position sensor, the sensor 106 measures a position of the subject over the time period.

In step 305, the data measured by the motion sensor 106 in step 303 is transmitted to the processor 108 and received at the processor 108. In one embodiment, the data transmitted in step 305 is the data that indicates the motion of the subject over the time period. In an example embodiment, where the data measured in step 303 is the acceleration of the subject over the time period, in step 305 the processor 108 converts the received acceleration data of the subject over the time period into motion data of the subject over the time period. In another example embodiment, where the data measured in step 303 is the position of the subject over the time period, in step 305 the processor 108 converts the received position data of the subject over the time period into motion data of the subject over the time period. In another example embodiment, the sensor 106 includes a processor that converts the acceleration data or position data into motion data prior to step 305.

In step 307, the processor 108 determines whether the value of the motion of the subject over the time period is less than a motion threshold. In one embodiment, the motion threshold is a motion of the subject indicative of the physiological parameter (e.g. heart rate, temperature, CO2 level) rising above a resting level of the physiological parameter or a threshold amount (e.g. 10%, 20% or more) above the resting level. In an example embodiment, the method further includes a step to measure the resting level of the physiological parameter (e.g. heart rate, temperature) of the subject. In this example embodiment, the physiological sensor (e.g. heart rate sensor 102, temperature sensor 104) is used to measure the physiological parameter of the subject over a certain time period (e.g. 30 seconds, 60 seconds) while the subject is at rest. In one embodiment, the resting level of the physiological parameter measured by the physiological sensor is stored in a memory of the processor 108. In another example embodiment, the method further includes a step to measure the motion threshold of the subject. In this example embodiment, the subject is positioned on an exercise machine (e.g. treadmill) and the physiological sensor (e.g. heart rate sensor 102, temperature sensor 104) measures the physiological parameter of the subject as the speed of the exercise machine is gradually increased from zero. When the value of the physiological parameter rises above the resting level previously measured and stored in the processor 108 memory or the threshold amount (e.g. 10%, 20% or more) above the resting level, the speed of the exercise machine (e.g. speed of the treadmill) is recorded as the motion threshold and stored in the memory of the processor 108. In another example embodiment, the motion sensor 106 is used to measure the value of the motion of the subject as the subject gradually increases a level of motion (e.g. from zero) and the motion threshold is determined as the measured value of the motion when the measured physiological parameter from the physiological sensor rises above the resting level or the threshold amount above the resting level. In an embodiment, the motion threshold is stored in a memory of the processor 108. In other embodiments, the motion threshold is predetermined. In an example embodiment, the motion threshold is in a range from 0-4 miles per hour (mph).

In one embodiment, in step 307 the processor 108 computes an average value of the motion of the subject over the time period and determines whether the average motion value is less than the motion threshold. In another embodiment, the data received in step 305 indicates the value of the motion of the subject at a plurality of time increments over the time period and in step 307 the processor determines whether the value of the motion at each time increment is less than the motion threshold. In an example embodiment, a positive determination in step 307 involves a position determination that the value of the motion at each time increment is less than the motion threshold.

A positive determination in step 307 moves the method to step 309. A negative determination in step 307 moves the method back to step 301.

In step 309, the data measured in step 301 by the physiological sensor indicating the change in the physiological parameter over the time period is transmitted to the processor 108 and received at the processor 108. In some embodiments, a negative determination in step 307 involves actively suppressing the transmission of the data measured in step 301 to the processor 108 so that the data is not received by the processor 108.

In step 311, the processor 108 determines whether the value of the change in the physiological parameter (based on the received data in step 309) is greater than a change threshold. In one embodiment, the change threshold is a minimum value of the change in the physiological parameter over the time period that is indicative of an adverse health condition (e.g. panic attack, heart attack, fast breathing, etc) of the subject. In some embodiments, the change threshold is based on a proportion (e.g. 20%, 50%, 100%) of the resting level of the physiological parameter for the subject that is measured in one embodiment of the method and stored in the memory of the processor 108. In one embodiment, where the data received in step 309 indicates a change in a value of a heart rate of the subject, in step 311 the processor 108 determines whether the value of the change in the heart rate over the time period exceeds a heart rate change threshold. In an example embodiment, the heart rate change threshold is a minimum value of the change in the heart rate over the time period that is indicative of the adverse health condition (e.g. panic attack, heart attack, fast breathing, etc) of the subject. In another embodiment, where the data received in step 309 indicates a change in a value of the body temperature of the subject, in step 311 the processor 308 determines whether the value of the change of the body temperature exceeds a temperature change threshold. In an example embodiment, the temperature change threshold is a minimum value of the change in the body temperature over the time period that is indicative of the adverse health condition (e.g. panic attack, heart attack, fast breathing, etc) of the subject. In yet another embodiment, where the data received in step 309 indicates a change in the value of the heart rate and the change in the value of the body temperature over the time period, in step 311 the processor 108 determines whether the value of the change in the heart rate exceeds the heart rate change threshold and whether the value of the change in the value of the body temperature exceeds the body temperature change threshold. In yet another embodiment, where the data received in step 309 indicates a change in a value of the CO2 level of the subject, in step 311 the processor 108 determines whether the value of the change in the CO2 level over the time period exceeds a CO2 change threshold. In an example embodiment, the CO2 change threshold is a minimum value of the change in the CO2 level over the time period that is indicative of the adverse health condition (e.g. panic attack, heart attack, fast breathing, etc) of the subject. In another example embodiment, the CO2 change threshold is based on the proportion (e.g. 20%, 50%, 100%) of the resting level of the CO2 level for the subject that was measured and stored in the memory of the processor 108.

A positive determination in step 311 moves the method to step 313. A negative determination in step 311 moves the method back to step 301.

In step 313, an action is performed based on the determination in step 311. In one embodiment, the determination in step 311 is used as a prediction of a health condition (e.g. panic attack, heart attack, fast breathing, etc) of the subject. In an embodiment, in step 313 one or more of steps 313a, 313b, 313c are performed. In some embodiments, all of the steps 313a, 313b, 313c are performed. In other embodiments, only one of the steps 313a, 313b, 313c is performed. In an embodiment, in steps 313a, 313b, the action is performed to alert the subject (or others) of the determination in step 311. In an embodiment, in step 313c, the action is performed to provide treatment (e.g. therapy, visual symbol) to the subject in response to the determination in step 311. In another embodiment, in step 313 the action performed is the processor 108 automatically calls or texts a designated phone number of a designated individual (e.g. family member, spouse, etc.) previously provided by the subject, to alert the designated individual of the prediction that the subject may develop the health condition. In yet another embodiment, in step 313 the action performed is the processor 108 automatically places a phone call to the mobile phone 601 of the subject, so that in the event that the subject is in a meeting, the subject can use the incoming phone call as a reason to exit the meeting and receive treatment for the possible health condition.

In step 313a, the processor 108 activates the haptic feedback device 110 worn by the subject (e.g. on the wrist strap 202) to alert the subject of the determination in step 311. In an example embodiment, in step 313a the haptic feedback device 110 generates mechanical stimulation (e.g. force, vibration, motion, etc.) that is detected by the subject. In another example embodiment, where the device 110 is an audible device that outputs an auditory alert, in step 313a the processor 108 activates the device 110 so that the auditory alert is detected by the subject. In one example embodiment, the haptic feedback device 110 is provided in the mobile phone 601 (e.g. activation of vibration mode in the mobile phone 601) and is activated to alert the subject of the determination in step 311. In another example embodiment, in step 313a the processor 108 activates the device 110 so that an audio output includes an audible reminder to the subject to recite their mission statement. In an example embodiment, in step 313a the audio output includes an audible output of the subject mission statement that is pre-selected, pre-recorded and stored in a memory of the processor 108. In yet another example embodiment, in step 313a the audio output includes an audible reminder to the subject to activate a kinesthetic touch or kinesthetic movement (e.g. placing two fingers together, a wrist movement, touching above the eyebrow, etc.) that the subject previously chose to make the subject feel more calm and centered. In an example embodiment, in step 313a the audio output includes an audible output of the subject's specific kinesthetic touch or movement (e.g. "activate your anchor", where "anchor" refers to the subject's specific kinesthetic movement) to further remind the subject. In another example embodiment, in step 313a the processor 108 activates the device 110 so that an audio output includes an audible reminder to the subject to visualize their symbol that they associate with being centered and calm. In an example embodiment, in step 313a the audio output includes an audible output of the subject's visual symbol that is pre-selected and stored in a memory of the processor 108.

In step 313b the processor 108 outputs one or more characters on a display device based on the determination in step 311 or to communicate the determination in step 311 or to communicate a prediction based on the determination in step 311. In one embodiment, the characters are output on the display device 111 of the assembly 100. In another embodiment, the characters are output on the display device 607 of the mobile phone 601. In an embodiment, the characters indicate an alert to the subject of a health condition (e.g. panic attack) based on the determination in step 311. In an example embodiment, the characters indicate the alert to the subject of a current health condition the subject is experiencing or a future health condition (e.g. panic attack) that the subject is not yet experiencing but that the subject is at risk of experiencing in the near future (e.g. within one hour). In another embodiment, the characters indicate the determination in step 311 (e.g. that the change in the heart rate exceeds the change threshold). In yet another embodiment, the characters indicate a suggested treatment for the possible adverse health condition (e.g. visualize their symbol, activate their anchor, recite their mission statement, taking medication, psychological stress therapy, contact emergency medical services, etc.). In some embodiments, in step 313b the processor 108 transmits a signal to a display device at a remote facility (e.g. a display device at an emergency medical facility) indicating the determination in step 311 to alert medical professionals at the remote facility of a possible adverse health condition based on the determination in step 311. In still other embodiments, in step 313b the processor 108 transmits a signal to the display device 111 or display device 607 to output a visual symbol that calms the subject when they observe the visual symbol. In some embodiments, the visual symbol is customized and chosen by the subject before the method 300 begins and stored in a memory of the processor 108. In an embodiment, the subject chooses the visual symbol based on a visual symbol which makes them feel centered and peaceful and into an alpha state that calms them down. In one example embodiment, the visual symbol is an animal or a nature scene (e.g. ocean). In one example embodiment, the method 300 includes a step before step 301 where the display device 111 or display device 607 outputs a plurality of symbols and the subject chooses one of the symbols which is stored in the memory of the processor 108 and output in step 313b as the visual symbol of the subject.

In step 313c, treatment is provided to the subject based on the determination in step 311. In one embodiment, the treatment is medical treatment designed to treat a health condition indicated by the determination in step 311. In an example embodiment, the treatment is psychological stress therapy designed to treat an adverse health condition (e.g. panic attack) indicated by the determination in step 311. In step 313c, the processor 108 automatically transmits a signal to a remote facility (e.g. medical facility) upon the determination in step 311, where the remote facility includes professionals that provide treatment. The signal includes location information of the subject and the determination in step 311. Upon receiving the signal at the remote facility, the professionals are either transported to the location of the subject and provide the treatment or arrange for transport of the subject to the remote facility where the subject is provided the treatment. In other embodiments, in step 313c the treatment involves the subject taking medication. In an example embodiment, in step 313c the processor 108 outputs a suggested medication and dosage to be taken by the subject in order to alleviate symptoms associated with the determination in step 311. In an example embodiment, the treatment involves the subject accessing treatment material, either with an app installed on the mobile phone 601 or through a website, where the treatment material includes audio tracks or videos (e.g. short tracks that are 5-10 minutes or longer tracks that are longer than 10 minutes) or live one on one interaction with a therapist or their visual symbol or their mission statement. In another example embodiment, the treatment involves the subject receiving a phone call on their mobile phone 601 from a therapist for one on one therapy.

In an embodiment, the method 300 includes steps to determine an effectiveness of a treatment or action in step 313 (e.g. in one or more of steps 313a, 313b, 313c). In some embodiments, the method 300 excludes steps 301-311 and the effectiveness of the action step 313 is assessed without steps 301-311. As depicted in FIG. 1, in one embodiment a sample 117 (e.g. body fluid such as blood, saliva, etc) is taken from the subject and measured by a device 114 to determine a value of one or more parameters of the sample 117 that indicate one or more levels of a biological parameter (e.g. hormones, cholesterol, proteins, biomarkers, comprehensive metabolic panel, etc) and/or a biological organ function of the subject. In an embodiment, the device 114 is any device appreciated by one of ordinary skill in the art that is used to measure the value of the one or more parameters from the biological sample 117 (e.g. body fluid, such as saliva or blood). In an example embodiment, the sample 117 is the subject that is scanned and the device 114 is a non-contact scanning device (e.g. AO Digital Body Analyzer® discussed in Example Embodiment section below). In an embodiment, the value of the parameters measured by the device 114 prior to the treatment step 313 are transmitted to the processor 108 and stored in the memory of the processor 108.

After the treatment step 313, a second sample 117 is obtained from the subject and measured by the device 114 to obtain a second value of the one or more parameters that indicate one or more levels of the biological parameters and/or biological organ function, after the treatment step 313. The value of the parameters measured by the device 114 after the treatment 313 is also transmitted to the processor 108 and stored in the memory of the processor 108. In some embodiments, the sample 117 is taken from the subject prior to and after the treatment step 313 and the two samples 117 are sent to a location remote from the assembly 100 (e.g. testing laboratory) where the device 114 is located, so the values of the parameters in the before and after samples 117 can be measured. In this example embodiment, the measured values of the parameters are subsequently communicated (e.g. using the network link 478 or input device 412 such as a flash drive) to the processor 108.

In an embodiment, to assess the effectiveness of the treatment step 313, the processor 108 compares the initial values of the one or more parameters from the sample 117 measured prior to the treatment step 313 with the second values of the one or more parameters from the second sample 117 measured after the treatment step 313. Additionally, the memory of the processor 108 has a normal value of the parameter stored in the memory. In an example embodiment, the processor 108 determines whether the treatment step 313 was effective, based on a change between the initial values of the parameters and the second values of the parameters and a normal value of the parameter. In an example embodiment, the processor 108 determines that the treatment step 313 is effective, based on the change in the value of the parameter (e.g. from 8 to 5) relative to a normal value (e.g. 4) of the parameter. In one embodiment, if the change in the value of the parameter is towards the normal value of the parameter (e.g. from 8 to 5, towards a normal value of 4), the processor 108 determines that treatment step 313 was effective. In an embodiment, the processor 108 is configured to output the determination of the effectiveness of the treatment step 313 on the display device 111. In an example embodiment, the processor 108 is configured to output a degree of effectiveness of the treatment step 313 on the display device 111 based on the magnitude of the change of the parameter relative to the normal value of the parameter. In an example embodiment, the processor 108 determines that a first change in the value of the parameter (e.g. from 8 to 5) from a first treatment step 313 is more effective than a second change in the value (e.g. from 8 to 6) from a second treatment step 313 that is less than the first change and/or where the first change results in a closer proximate value (e.g. 5) to the normal value (e.g. 4) than the second change (e.g. 6).

In an embodiment, the method 300 further includes performing further action (e.g. further treatment or action steps 313 or 363) based on the effectiveness of the first treatment or action steps 313 or 363. In an example embodiment, if the change in the value of the parameter (e.g. cortisol) from the first treatment step 313 resulted in a change from a high level (e.g. 8) to a level (e.g. 5) that is still above a normal level (e.g. 4), the processor 108 can determine that further action such as further treatment steps 313 or 363 should be performed. In an example embodiment, the processor 108 outputs the recommended subsequent treatment step 313 or 363 and/or the effectiveness of the initial treatment step 313 or 363 that formed the basis of the suggestion for the subsequent treatment 313 or 363.

FIG. 3B is a flow chart that illustrates an example method 350 for automatically monitoring a physiological parameter of a subject, according to an embodiment. In step 351, data is measured with a first physiological sensor that indicates a change in a value of a first physiological parameter of the subject over a time period. In one embodiment, the first physiological sensor is the heart rate sensor 102 that measures data that indicates a change in a value of the heart rate of the subject over the time period. In another embodiment, the first physiological sensor is the temperature sensor 104 that measures data that indicates a change in a value of the body temperature of the subject over the time period. In yet another embodiment, the first physiological sensor is the CO2 sensor 105 that measures data that indicates a change in the level of CO2 in the breath of the subject over the time period.

In step 353, data is measured with a second physiological sensor that indicates a change in a value of a second physiological parameter of the subject over a time period. In one embodiment, the second physiological sensor is the temperature sensor 104 that measures data that indicates a change in a value of the body temperature of the subject over the time period. In another embodiment, the second physiological sensor is the heart rate sensor 102 that measures data that indicates a change in a value of the heart rate of the subject over the time period. In yet another embodiment, the second physiological sensor is the CO2 sensor 105 that measures data that indicates a change in the level of CO2 in the breath of the subject over the time period.

In step 355, the data measured by the first physiological sensor (e.g. heart rate sensor 102) in step 351 is transmitted to the processor 108 and received at the processor 108.

In step 357, the processor 108 determines whether the value of the change of the first physiological parameter (e.g. value of the change of the heart rate) over the time period is greater than a first change threshold. In one embodiment, the first change threshold of the first physiological parameter is determined in a similar manner as the change threshold in step 311 is determined.

A positive determination in step 357 moves the method to step 359. A negative determination in step 357 moves the method back to step 351.

In step 359, the data measured in step 353 by the second physiological sensor indicating the change in the second physiological parameter over the time period is transmitted to the processor 108 and received at the processor 108. In some embodiments, a negative determination in step 357 involves actively suppressing the transmission of the data measured in step 353 to the processor 108 so that the data is not received by the processor 108.

In step 361, the processor 108 determines whether the value of the change in the second physiological parameter (based on the received data in step 359) is greater than a second change threshold. In one embodiment, the second change threshold of the second physiological parameter is determined in a similar manner as the change threshold in step 311 is determined. In one embodiment, where the data received in step 359 indicates a change in a value of the body temperature of the subject, in step 361 the processor 108 determines whether the value of the change in the body temperature over the time period exceeds a temperature change threshold.

A positive determination in step 361 moves the method to step 363. A negative determination in step 361 moves the method back to step 351. In an embodiment, step 363 involves an action performed based on the determination in step 361 in a similar manner as the action performed in step 313 based on the determination in step 311. In one embodiment, steps 363a, 363b, 363c are similar to steps 313a, 313b, 313c previously discussed.

In another embodiment, the action performed in step 363 involves measuring a level of physical activity of the subject using the motion sensor 102. In an example embodiment, the level of physical activity of the subject is measured over the time period. In another example embodiment, the level of physical activity of the subject is measured over a subsequent time period following the time period during which the data is measured in steps 351 and 353. In an example embodiment, the measurement of the level of physical activity in step 363 is similar to step 307 (e.g. determining whether the motion of the subject is less than a motion threshold). In an example embodiment, a determination of a lack of physical activity of the subject (e.g. determining that the motion of the subject is less than the motion threshold) causes additional action to be performed, such as one or more of steps 363a, 363b, 363c.

In an embodiment, the method 350 includes steps to determine an effectiveness of a treatment or action in step 363 (e.g. in one or more of steps 363a, 363b, 363c) that is similar to the above steps to determine the effectiveness of the treatment or action in step 313.

2. Example Embodiments

According to an example embodiment, the assembly 100 is used to predict the onset of an adverse health condition in the subject, such as a panic attack. In one embodiment, a panic attack is a sudden period of intense fear that may include palpitations, sweating, shaking, shortness of breath, numbness, or a feeling that something bad is going to happen.

Subjects with panic attacks often report a fear of dying or heart attack, flashing vision, faintness or nausea, numbness throughout the body, heavy breathing and hyperventilation, or loss of body control. Some people also suffer from tunnel vision, mostly due to blood flow leaving the head to more critical parts of the body in defense. These feelings may provoke a strong urge to escape or flee the place where the attack began (a consequence of the "fight-or-flight response", in which the hormone causing this response is released in significant amounts). This response floods the body with hormones, particularly epinephrine (adrenaline), which aid it in defending against harm. A panic attack is a response of the sympathetic nervous system (SNS). The most common symptoms of panic attacks include trembling, dyspnea (shortness of breath), heart palpitations, chest pain (or chest tightness), hot flashes, cold flashes, burning sensations (particularly in the facial or neck area), sweating, nausea, dizziness (or slight vertigo), light-headedness, hyperventilation, paresthesias (tingling sensations), sensations of choking or smothering, difficulty moving, and derealization. In an example embodiment, any physiological sensor capable of measuring a physiological parameter associated with any of these symptoms can be used for the sensors 102, 104, 105 in the assembly 100.

In an example embodiment, the treatment provided in step 313c or 363c can include one or more of the treatments discussed herein. In some embodiments, panic attacks can be effectively treated with a variety of interventions, including psychological therapies and medication. In an example embodiment, the psychological therapy is cognitive behavioral therapy followed by specific selective serotonin reuptake inhibitors. In another example embodiment, the psychological therapy is psychoanalytic psychotherapy for relieving panic attacks. In some embodiments, the treatment involves providing anxiolytic medication, such as benzodiazepines. In other embodiments, the treatment involves breathing exercises. In an example embodiment, in cases where hyperventilation is involved, deliberate deep breathing exercises help to rebalance the oxygen and CO2 levels in the blood. In an example embodiment, the treatment involves recommendation of breathing exercises such as a 5-2-5 count. Using the stomach (or diaphragm)—and not the chest—inhale (feel the stomach come out, as opposed to the chest expanding) for 5 seconds. As the maximal point at inhalation is reached, hold the breath for 2 seconds. Then slowly exhale, over 5 seconds. Repeat this cycle twice and then breathe 'normally' for 5 cycles (1 cycle=1 inhale+1 exhale). The point is to focus on the breathing and relax the heart rate. Regular diaphragmatic breathing may be achieved by extending the outbreath by counting or humming. In an example embodiment, in step 313c or 363c, directions for the breathing exercises may be output on the display device 111 or 607 or breathing exercise instructions may be audibly output using audio speakers on the mobile phone 601.

In some embodiments, the treatment provided in step 313c or 363c includes a combination of cognitive and behavioral therapies. In some embodiments, medication might also be appropriate in the treatment provided in step 313c or 363c. In an example embodiment, the first part of therapy is largely informational; many subjects are greatly helped by simply understanding exactly what the panic attack is and how many others suffer from it. Many subjects who suffer from panic attacks are worried that their panic attacks mean they are "going crazy" or that the panic might induce a heart attack. Cognitive restructuring helps subjects replace those thoughts with more realistic, positive ways of viewing the panic attacks. In another example embodiment, the treatment provided in step 313c or 363c may include exposure therapy, which includes repeated and prolonged confrontation with feared situations and body sensations, to help weaken anxiety responses to these external and internal stimuli and reinforce realistic ways of viewing panic symptoms. In yet another example embodiment, the treatment provided in step 313c or 363c may include deeper level psychoanalytic approaches, in particular object relations theory. Panic attacks are frequently associated with splitting (psychology), paranoid-schizoid and depressive positions, and paranoid anxiety. They are often found comorbid with borderline personality disorder and child sexual abuse. Paranoid anxiety may reach the level of a persecutory anxiety state.

In yet another example embodiment, the treatment provided in step 313c or 363c may include meditation that may also be helpful in the treatment of panic disorders. The processor 108 may output meditation instructions on the display device 111 or 607 or may output meditation audio instruction or music on an audio speaker of the mobile phone 601.

In yet another example embodiment, the treatment provided in step 313c or 363c may include dietary changes. In an example embodiment, the processor 108 may output dietary suggestions to the display device 111 or 607 such as reduction of consumption of one or more substances (e.g. caffeine) that may cause or exacerbate panic anxiety. Anxiety can temporarily increase during withdrawal from caffeine and various other drugs.

In yet another example embodiment, the treatment provided in step 313c or 363c may include exercise. In an example embodiment, the processor 108 may output a suggested exercise regimen to the display device 111 or 607. Increased and regimented aerobic exercise (e.g. running) has been shown to have a positive effect in combating panic anxiety. There is evidence that suggests that this effect is correlated to the release of exercise-induced endorphins and the subsequent reduction of the stress hormone cortisol. There remains a chance of increased respiration rate that occurs during aerobic exercise. However, step 307 of the method 300 advantageously suppresses consideration of physiological data values during exercise. Benefits of incorporating an exercise regimen have shown best results when paced accordingly.

In some embodiments, panic attacks do not strike subjects without warning, as discussed in *Subtle Signs Warn of Panic Attacks in Advance*, SMU Research News, Jul. 26, 2011 (hereinafter referred to as "Nauert, 2011"), which is incorporated by reference herein. The values of one or more physiological parameters of a subject are elevated for a time period (e.g. up to one hour) prior to subject being aware of the panic attack (Nauert, 2011). In many subjects, they are not aware of the elevation of the physiological parameters during this time period prior to awareness of the panic attack (Nauert, 2011). The assembly 100 and methods 300, 350 discussed herein advantageously alerts the subject during this time period, so that the subject becomes aware of a possible impending panic attack, up to one hour prior to actual onset of the panic attack. Also, the method 300 or 350 advantageously provides treatment in steps 313c or 363c during this time period, so to assist in alleviating symptoms of the panic attack (e.g. elevated physiological parameters) prior to onset of the panic attack and thus increasing the likelihood that the panic attack will be thwarted.

In some embodiments, the inventor recognized that it would be effective to use a physical parameter that could be used to measure the effectiveness of one or more treatment or action steps discussed herein. In an embodiment, the physical parameter can be used to measure an effectiveness of the treatment step 313 (e.g. one or more of steps 313a, 313b, 313c) or treatment step 363 (e.g. one or more of steps 363a, 363b, 363c). Thus, the inventor developed the concept of performing an initial measurement (e.g. scan) of a value of a parameter that indicates one or more biomarkers and/or biological parameters and/or biological organ function prior to and after the treatment step 313. The inventor recognized that this would advantageously provide physical criteria (e.g. the difference between the measured parameters before and after the treatment step) as an indication of the effectiveness of the treatment.

The inventor recognized that unresolved trauma creates inflammation in the body and this inflammation manifests in the body as a "pause" or freeze state that the body enters until the perceived danger passes. On a cellular level, one indicator of this "pause" state in the body is a hardened cellular membrane which prevents foreign invading substances from entering the cell and consequently also prevents necessary carriers from exiting the cell, thereby inhibiting healthy cell maintenance. The body stays in this "pause" state since the memory of the subject continues to loop the unresolved trauma and thus the inflammation remains persistent. The inventor recognized that this results in autoimmune problems since it affects the autoimmune system and the neurotransmitters. The inventor recognized that conventional methods that address the inflammation and "pause" condition in the body (e.g. medication) do not resolve this issue since they only temporarily resolve the "pause" state. Hence the inflammation and "pause" state resume once the medication wears off and thus the medication merely provides a temporary solution with addressing the underlying cause (e.g. looping of unresolved trauma) of the inflammation and "pause" state.

In one embodiment, one or more of the treatment steps 313 or 363 (313a, 313b, 313c, 363a, 363b, 363c) help to stop the subject memory from looping the unresolved trauma, so that the inflammation is reduced and hence the "pause" state ends and the cells open up, permitting healthy cellular maintenance to resume. The inventor realized that this could be confirmed by the measurement of the parameter values with the device 114 before and after the treatment step 313 or 363 and then comparing the before and after parameter values. In one example embodiment, the parameter is cholesterol and a male subject had a high cholesterol value (e.g. 8 on a scale of 1-9) prior to the treatment step 313 (e.g. 4 hour session) and a much lower cholesterol value (e.g. 5, where 4 is normal) after the treatment step 313. In an example embodiment, the 1-9 scale is used by the AO Digital Body Analyzer®, discussed below. The inventor subsequently realized that the reason for the reduction in the cholesterol was the mobilization of cholesterol due to the opening of the cellular membrane due to the reduction of inflammation from the memory of the subject no longer looping the unresolved trauma, as a result of the treatment step 313. After the inflammation in the subject reduced, cholesterol was released from the cells and was processed by the liver into biosalts to cleanse the intestines. In another example embodiment, the parameter is cortisol and a change in the value of the cortisol is measured prior to and after the treatment step 313. In yet another example embodiment, parameters including amino acids and digestive system function are measured by the device 114 before and after the treatment step 313 to determine the effectiveness of the treatment step 313. The inventor recognized that subjects with past trauma and/or whose memory loops these past trauma events typically have high cortisol levels and thus the inventor recognized that measuring the level of cortisol before and after the treatment steps 313 or 363 is useful to measure an effectiveness of the treatment steps 313 or 363. In yet another embodiment, the parameter is amyloid and a change in the value of amyloid is measured prior to and after the treatment step 313 or 363. The inventor recognized that amyloid is a byproduct that thickens the viscosity of blood to try and slow down blood flow and is a stress related hormone that is elevated when the memory of the subject loops unresolved trauma and during the "pause" state. Thus, the inventor recognized that measuring the level of amyloid before and after the treatment steps 313 or 363 is useful to measure an effectiveness of the treatment steps 313 or 363.

Figure 7:
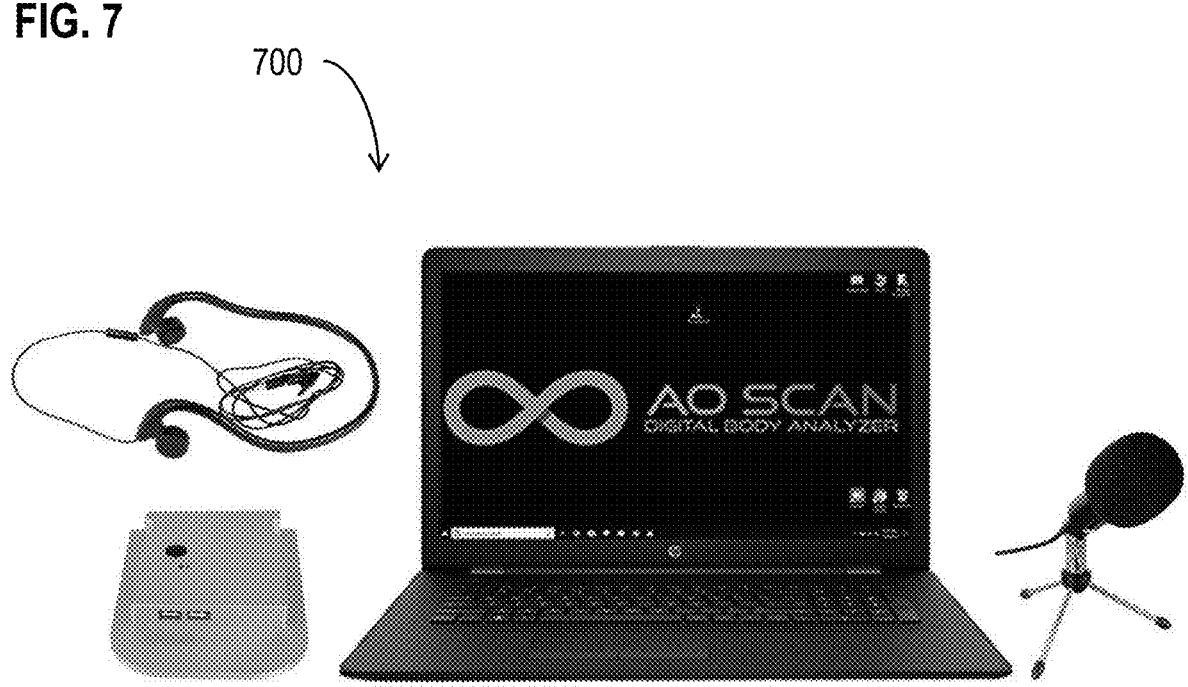
FIG. 7 is an image that illustrates example components of a device of the assembly of FIG. 1 used to measure parameter values of the sample, according to an embodiment.

In an embodiment, the sample 117 is the subject and the device 114 that is used to measure the value of the one or more parameters is an AO Digital Body Analyzer® 700, that is manufactured by AO Scan of Orem, Utah. FIG. 7 illustrates an example embodiment of the AO Digital Body Analyzer 700. The AO Scan Digital Body Analyzer® 700 is a combination of technology from Russia, Germany, Spain, Asia and the USA. Most if not all this technology is based on the works of Nikola Tesla, Dr. Royal Rife, Albert Einstein and others that theorize everything physical at its most fundamental level is actually energy frequency. Biophysicists in Germany and Russia pioneered the work of identifying specific frequencies in the human body and compiled a database of more than 120,000 different frequencies. These frequencies are the same in most people. Medical researchers in Germany believe that the health of an organ, tissue, system or cell structure within the body can be identified by passing micro current frequencies through the body and measuring the current's resistance.

In an embodiment, the scan performed by the AO Digital Body Analyzer 700 is safe and noninvasive; shows greater detail (unique amongst all non-invasive scanners); lists the detailed anatomy or components of each item that it scans and is a simple method for measuring the health state of the entire body. The AO Digital Body Analyzer 700 is an electronic device that is capable of measuring these oscillations or frequencies utilizing the AO Scan Bio-Transduring Headset. Additionally, the AO Digital Body Analyzer 700 presents detailed visual reports of the health status of the organs, systems, and tissue of the body, working similarly to other scanners in principles of measuring electromagnetic signals and the subtle bio-frequencies. Every cell and organ in the body has its own distinctive vibrational frequency or oscillation. When these oscillations are disrupted, whether by injury, diet, stress or emotion, it results in a disruption of that biological function. Which when not addressed, can bring about fatigue, depression, illness, disease and even death. Over the past 20 years, more than 120,000 of these vibrational frequencies have been isolated, identified and cataloged. Knowing what the optimum oscillation or frequencies of these cells and organs are, can assist in determining the root cause of an individual's health status when these frequencies are compared to the individual scanned results.

When initiating a scan with the AO Digital Body Analyzer 700, specific frequencies for the item being scanned are introduced to the brain. The brain then responds with what that item is actually resonating at. The introduced frequencies are then compared to the actual frequencies. A numerical value is then determined, where the numerical values range from 1-9, with 5 indicating that the item is in balance. The lower numbers, 4-1 generally indicate an underactive or lethargic condition. The higher numbers, 6-9 generally indicate an overactive or stressed condition. These signals are then converted into algorithms within the AO Scan system, compared to an extensive database, and then are graphically displayed. Once the scan is complete, a 24-page report is produced. This report divides 650+ areas into 47 categories like environmental and food allergies, bacterial, viral, fungal and parasitic diseases, heavy metals, genetic problems, hormonal problems, GI problems, eye health, kidney function, and reproductive function. The report also specifically looks into amino acids, vitamins, minerals, parasitic load, and collagen index; this information helps to determine the correct nutraceuticals that are needed to bring the body back into balance.

FIG. 8 depicts a Table that includes a sample scan (using the 1-9 number scale) for a number of biological parameters (e.g. amino acids, hormones, proteins, organ function, etc). In an embodiment, the Table of FIG. 8 shows a "pre" and "post" scan for a number of patients along the top row, where "pre" scan is the scan of the subject prior to the treatment step 313 or 363 and the "post" is the scan of the subject after the treatment step 313 or 363. The vertical columns lists the biological parameters (e.g. amino acids, hormones, proteins, organ function, etc) whose values were measured by the "pre" and "post" scan. As depicted in the Table of FIG. 8, for many of the subjects, much of the values of the biological parameters improved (e.g. moved closer to normal value of 5) between the "pre" and "post" scans. In an example embodiment, particularly for those biological parameters indicative of stress and trauma (e.g. cortisol), in most subjects the values of the cortisol moved closer to the normal value (e.g. 5) from the pre to the post scans. Thus, this data provides indication that the treatment step 313 or 363 were effectiveness based on physical criteria and/or that the treatment step 313 or 363 had positive effects on the physical health of the patient.

As shown in the Table of FIG. 8, the parameters whose values are measured by the AO Digital Body Analyzer include one or more of emotional stability; mental clarity; vagal tone; HDL-C; LDL-C Direct; Neutral Fat; Non HDL C; Total Cholesterol; Triglycerides; Albumin; Circulating Immune Complex; Ferritin; Rheumatism; Cranial Nerve 10 Vagus Nerve; Parasympathetic NS Function; Sympathetic NS Function; Adrenal Complex; Thyroid; Gastric Absorption; Cortisol; GABA; Serotonin; Cortisol Dysfunction; Cytokine Activity; Fibrinogen; HS-CRP; Homocysteine; Histamine; Lp-PLA2; Myeloperoxidase; nf-Kappa b; Sedimentation Rate; Leptin; Bile Secretion Function. In some embodiments, more parameters other than those listed above are measured by the AO Digital Body analyzer. In still other embodiments, some of the parameters listed above are measured by a device 114 other than the AO Digital Body analyzer, either a scanner (e.g. where the subject is used for the sample 117) or a device which measures the parameter values in a sample 117 that is collected before and after the treatment step 313 or 363.

3. Hardware Overview

FIG. 4 is a block diagram that illustrates a computer system 400 upon which an embodiment of the invention may be implemented. Computer system 400 includes a communication mechanism such as a bus 410 for passing information between other internal and external components of the computer system 400. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 400, or a portion thereof, constitutes a means for performing one or more steps of one or more methods described herein.

A sequence of binary digits constitutes digital data that is used to represent a number or code for a character. A bus 410 includes many parallel conductors of information so that information is transferred quickly among devices coupled to the bus 410. One or more processors 402 for processing information are coupled with the bus 410. A processor 402 performs a set of operations on information. The set of operations include bringing information in from the bus 410 and placing information on the bus 410. The set of operations also typically include comparing two or more units of information, shifting positions of units of information, and combining two or more units of information, such as by addition or multiplication. A sequence of operations to be executed by the processor 402 constitutes computer instructions.

Computer system 400 also includes a memory 404 coupled to bus 410. The memory 404, such as a random access memory (RAM) or other dynamic storage device, stores information including computer instructions. Dynamic memory allows information stored therein to be changed by the computer system 400. RAM allows a unit of information stored at a location called a memory address to be stored and retrieved independently of information at neighboring addresses. The memory 404 is also used by the processor 402 to store temporary values during execution of computer instructions. The computer system 400 also includes a read only memory (ROM) 406 or other static storage device coupled to the bus 410 for storing static information, including instructions, that is not changed by the computer system 400. Also coupled to bus 410 is a non-volatile (persistent) storage device 408, such as a magnetic disk or optical disk, for storing information, including instructions, that persists even when the computer system 400 is turned off or otherwise loses power.

Information, including instructions, is provided to the bus 410 for use by the processor from an external input device 412, such as a keyboard containing alphanumeric keys operated by a human user, or a sensor. A sensor detects conditions in its vicinity and transforms those detections into signals compatible with the signals used to represent information in computer system 400. Other external devices coupled to bus 410, used primarily for interacting with humans, include a display device 414, such as a cathode ray tube (CRT) or a liquid crystal display (LCD), for presenting images, and a pointing device 416, such as a mouse or a trackball or cursor direction keys, for controlling a position of a small cursor image presented on the display 414 and issuing commands associated with graphical elements presented on the display 414.

In the illustrated embodiment, special purpose hardware, such as an application specific integrated circuit (IC) 420, is coupled to bus 410. The special purpose hardware is configured to perform operations not performed by processor 402 quickly enough for special purposes. Examples of application specific ICs include graphics accelerator cards for generating images for display 414, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 400 also includes one or more instances of a communications interface 470 coupled to bus 410. Communication interface 470 provides a two-way communication coupling to a variety of external devices that operate with their own processors, such as printers, scanners and external disks. In general the coupling is with a network link 478 that is connected to a local network 480 to which a variety of external devices with their own processors are connected. For example, communication interface 470 may be a parallel port or a serial port or a universal serial bus (USB) port on a personal computer. In some embodiments, communications interface 470 is an integrated services digital network (ISDN) card or a digital subscriber line (DSL) card or a telephone modem that provides an information communication connection to a corresponding type of telephone line. In some embodiments, a communication interface 470 is a cable modem that converts signals on bus 410 into signals for a communication connection over a coaxial cable or into optical signals for a communication connection over a fiber optic cable. As another example, communications interface 470 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 470 sends and receives electrical, acoustic or electromagnetic signals, including infrared and optical signals, that carry information streams, such as digital data.

The term computer-readable medium is used herein to refer to any medium that participates in providing information to processor 402, including instructions for execution. Such a medium may take many forms, including, but not limited to, non-volatile media, volatile media and transmission media. Non-volatile media include, for example, optical or magnetic disks, such as storage device 408. Volatile media include, for example, dynamic memory 404. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 402, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 402, except for carrier waves and other signals.

Logic encoded in one or more tangible media includes one or both of processor instructions on a computer-readable storage media and special purpose hardware, such as ASIC *420.

Network link 478 typically provides information communication through one or more networks to other devices that use or process the information. For example, network link 478 may provide a connection through local network 480 to a host computer 482 or to equipment 484 operated by an Internet Service Provider (ISP). ISP equipment 484 in turn provides data communication services through the public, world-wide packet-switching communication network of networks now commonly referred to as the Internet 490. A computer called a server 492 connected to the Internet provides a service in response to information received over the Internet. For example, server 492 provides information representing video data for presentation at display 414.

The invention is related to the use of computer system 400 for implementing the techniques described herein. According to one embodiment of the invention, those techniques are performed by computer system 400 in response to processor 402 executing one or more sequences of one or more instructions contained in memory 404. Such instructions, also called software and program code, may be read into memory 404 from another computer-readable medium such as storage device 408. Execution of the sequences of instructions contained in memory 404 causes processor 402 to perform the method steps described herein. In alternative embodiments, hardware, such as application specific integrated circuit 420, may be used in place of or in combination with software to implement the invention. Thus, embodiments of the invention are not limited to any specific combination of hardware and software.

The signals transmitted over network link 478 and other networks through communications interface 470, carry information to and from computer system 400. Computer system 400 can send and receive information, including program code, through the networks 480, 490 among others, through network link 478 and communications interface 470. In an example using the Internet 490, a server 492 transmits program code for a particular application, requested by a message sent from computer 400, through Internet 490, ISP equipment 484, local network 480 and communications interface 470. The received code may be executed by processor 402 as it is received, or may be stored in storage device 408 or other non-volatile storage for later execution, or both. In this manner, computer system 400 may obtain application program code in the form of a signal on a carrier wave.

Various forms of computer readable media may be involved in carrying one or more sequence of instructions or data or both to processor 402 for execution. For example, instructions and data may initially be carried on a magnetic disk of a remote computer such as host 482. The remote computer loads the instructions and data into its dynamic memory and sends the instructions and data over a telephone line using a modem. A modem local to the computer system 400 receives the instructions and data on a telephone line and uses an infra-red transmitter to convert the instructions and data to a signal on an infra-red a carrier wave serving as the network link 478. An infrared detector serving as communications interface 470 receives the instructions and data carried in the infrared signal and places information representing the instructions and data onto bus 410. Bus 410 carries the information to memory 404 from which processor 402 retrieves and executes the instructions using some of the data sent with the instructions. The instructions and data received in memory 404 may optionally be stored on storage device 408, either before or after execution by the processor 402.

FIG. 5 illustrates a chip set 500 upon which an embodiment of the invention may be implemented. Chip set 500 is programmed to perform one or more steps of a method described herein and includes, for instance, the processor and memory components described with respect to FIG. *4 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 500, or a portion thereof, constitutes a means for performing one or more steps of a method described herein.

In one embodiment, the chip set 500 includes a communication mechanism such as a bus 501 for passing information among the components of the chip set 500. A processor 503 has connectivity to the bus 501 to execute instructions and process information stored in, for example, a memory 505. The processor 503 may include one or more processing cores with each core configured to perform independently. A multi-core processor enables multiprocessing within a single physical package. Examples of a multi-core processor include two, four, eight, or greater numbers of processing cores. Alternatively or in addition, the processor 503 may include one or more microprocessors configured in tandem via the bus 501 to enable independent execution of instructions, pipelining, and multithreading. The processor 503 may also be accompanied with one or more specialized components to perform certain processing functions and tasks such as one or more digital signal processors (DSP) 507, or one or more application-specific integrated circuits (ASIC) 509. A DSP 507 typically is configured to process real-world signals (e.g., sound) in real time independently of the processor 503. Similarly, an ASIC 509 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 503 and accompanying components have connectivity to the memory 505 via the bus 501. The memory 505 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 505 also stores the data associated with or generated by the execution of one or more steps of the methods described herein.

FIG. 6 is a diagram of exemplary components of a mobile terminal 600 (e.g., cell phone handset) for communications, which is capable of operating in the system of FIG. 2C, according to one embodiment. In some embodiments, mobile terminal 601, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 603, a Digital Signal Processor (DSP) 605, and a receiver/transmitter unit including a microphone gain control unit and a speaker gain control unit. A main display unit 607 provides a display to the user in support of various applications and mobile terminal functions that perform or support the steps as described herein. The display 607 includes display circuitry configured to display at least a portion of a user interface of the mobile terminal (e.g., mobile telephone). Additionally, the display 607 and display circuitry are configured to facilitate user control of at least some functions of the mobile terminal. An audio function circuitry 609 includes a microphone 611 and microphone amplifier that amplifies the speech signal output from the microphone 611. The amplified speech signal output from the microphone 611 is fed to a coder/decoder (CODEC) 613.

A radio section 615 amplifies power and converts frequency in order to communicate with a base station, which is included in a mobile communication system, via antenna 617. The power amplifier (PA) 619 and the transmitter/modulation circuitry are operationally responsive to the MCU 603, with an output from the PA 619 coupled to the duplexer 621 or circulator or antenna switch, as known in the art. The PA 619 also couples to a battery interface and power control unit 620.

In use, a user of mobile terminal 601 speaks into the microphone 611 and his or her voice along with any detected background noise is converted into an analog voltage. The analog voltage is then converted into a digital signal through the Analog to Digital Converter (ADC) 623. The control unit 603 routes the digital signal into the DSP 605 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 625 for compensation of any frequency-dependent impairments that occur during transmission though the air such as phase and amplitude distortion. After equalizing the bit stream, the modulator 627 combines the signal with a RF signal generated in the RF interface 629. The modulator 627 generates a sine wave by way of frequency or phase modulation. In order to prepare the signal for transmission, an up-converter 631 combines the sine wave output from the modulator 627 with another sine wave generated by a synthesizer 633 to achieve the desired frequency of transmission. The signal is then sent through a PA 619 to increase the signal to an appropriate power level. In practical systems, the PA 619 acts as a variable gain amplifier whose gain is controlled by the DSP 605 from information received from a network base station. The signal is then filtered within the duplexer 621 and optionally sent to an antenna coupler 635 to match impedances to provide maximum power transfer. Finally, the signal is transmitted via antenna 617 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 601 are received via antenna 617 and immediately amplified by a low noise amplifier (LNA) 637. A down-converter 639 lowers the carrier frequency while the demodulator 641 strips away the RF leaving only a digital bit stream. The signal then goes through the equalizer 625 and is processed by the DSP 605. A Digital to Analog Converter (DAC) 643 converts the signal and the resulting output is transmitted to the user through the speaker 645, all under control of a Main Control Unit (MCU) 603 which can be implemented as a Central Processing Unit (CPU) (not shown).

The MCU 603 receives various signals including input signals from the keyboard 647. The keyboard 647 and/or the MCU 603 in combination with other user input components (e.g., the microphone 611) comprise a user interface circuitry for managing user input. The MCU 603 runs a user interface software to facilitate user control of at least some functions of the mobile terminal 601 as described herein. The MCU 603 also delivers a display command and a switch command to the display 607 and to the speech output switching controller, respectively. Further, the MCU 603 exchanges information with the DSP 605 and can access an optionally incorporated SIM card 649 and a memory 651. In addition, the MCU 603 executes various control functions required of the terminal. The DSP 605 may, depending upon the implementation, perform any of a variety of conventional digital processing functions on the voice signals. Additionally, DSP 605 determines the background noise level of the local environment from the signals detected by microphone 611 and sets the gain of microphone 611 to a level selected to compensate for the natural tendency of the user of the mobile terminal 601.

The CODEC 613 includes the ADC 623 and DAC 643. The memory 651 stores various data including call incoming tone data and is capable of storing other data including music data received via, e.g., the global Internet. The software module could reside in RAM memory, flash memory, registers, or any other form of writable storage medium known in the art. The memory device 651 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 649 carries, for instance, important information, such as the cellular phone number, the carrier supplying service, subscription details, and security information. The SIM card 649 serves primarily to identify the mobile terminal 601 on a radio network. The card 649 also contains a memory for storing a personal telephone number registry, text messages, and user specific mobile terminal settings.

In some embodiments, the mobile terminal 601 includes a digital camera comprising an array of optical detectors, such as charge coupled device (CCD) array 665. The output of the array is image data that is transferred to the MCU for further processing or storage in the memory 651 or both. In the illustrated embodiment, the light impinges on the optical array through a lens 663, such as a pin-hole lens or a material lens made of an optical grade glass or plastic material. In the illustrated embodiment, the mobile terminal 601 includes a light source 661, such as a LED to illuminate a subject for capture by the optical array, e.g., CCD 665. The light source is powered by the battery interface and power control module 620 and controlled by the MCU 603 based on instructions stored or loaded into the MCU 603.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

4. References

Nauert, Rick Ph.D, *Subtle Signs Warn of Panic Attacks in Advance*, SMU Research News, Jul. 26, 2011.

What is claimed is:

1. An assembly for detecting a current or future panic attack, anxiety episode, or post-traumatic stress disorder (PTSD) flashback, comprising:
    at least one physiological sensor configured to measure data that indicates a change in a value of at least one physiological parameter of a subject over a time period;
    a motion sensor configured to measure data that indicates a value of a motion of the subject over the time period;
    a device configured to alert the subject of the current or future panic attack, anxiety episode, or post-traumatic stress disorder (PTSD) flashback;
    at least one processor; and
    at least one memory including one or more sequences of instructions, the at least one memory and the one or more sequences of instructions configured to, with the at least one processor, cause the assembly to perform at least the following;
    receive data from the motion sensor;
    determine whether the value of the motion of the subject over the time period is less than a motion threshold;
    receive data from the at least one physiological sensor over the time period if the value of the motion of the subject is less than the motion threshold;
    determine whether the change in the value of the at least one physiological parameter over the time period exceeds a change threshold, said determination being indicative of the current or future panic attack, anxiety episode, or PTSD flashback; and
    perform an action based on the determination that the change in the value of the at least one physiological parameter exceeds the change threshold comprising activation, of the device to prompt the subject to take action to treat the current panic attack, anxiety episode, or PTSD flashback or prevent onset of the future panic attack, anxiety episode, or PTSD flashback.

2. An assembly as claimed in claim 1, wherein the physiological sensor is a heart rate sensor and wherein the physiological parameter is a heart rate of the subject.

3. An assembly as claimed in claim 1, wherein the physiological sensor is a temperature sensor and wherein the physiological parameter is a body temperature of the subject.

4. An assembly as claimed in claim 1, wherein the at least one physiological sensor comprises a heart rate sensor and a temperature sensor; and wherein the at least one physiological parameter comprises a heart rate and a body temperature of the subject.

5. An assembly as claimed in claim 1, wherein the motion sensor is one of:
an accelerometer, wherein the data indicates a value of an acceleration of the subject over the time period and wherein the memory and sequence of instruction is further configured to cause the assembly to determine the value of the motion of the subject over the time period based on the value of the acceleration of the subject over the time period; and
a position sensor, wherein the data indicates a value of a position of the subject over the time period and wherein the memory and sequence of instruction is further configured to cause the assembly to determine the value of the motion of the subject over the time period based on the value of the position of the subject over the time period.

6. An assembly as claimed in claim 1, wherein at least one of the physiological sensor and the motion sensor is worn on a body of the subject.

7. An assembly as claimed in claim 6, wherein the at least one of the physiological sensor and the motion sensor is worn on a wrist of the subject.

8. An assembly as claimed in claim 1, wherein the device is a haptic feedback device and wherein the action performed includes activation of the haptic feedback device to alert the subject of the determination that the change in the value of the at least one physiological parameter exceeds the change threshold.

9. An assembly as claimed in claim 1, wherein the device is a display device and wherein the action performed is an output of one or more characters on the display device based on the determination that the change in the value of the at least one physiological parameter exceeds the change threshold.

10. An assembly as claimed in claim 1, further comprising a rechargeable battery to provide electrical power to the at least one of the physiological sensor, the motion sensor and the processor.

11. The assembly as claimed in claim 1, wherein the device is at least one of:
a phone, wherein the activation of the device comprises automatically calling or texting a designated phone number of the subject or a designated individual to alert the subject or the designated individual of the current or future panic attack, anxiety episode, or PTSD flashback;
a haptic feedback device, wherein the activation of the device comprises generating mechanical stimulation configured to be detected by the subject to prompt the subject to take an action that was previously selected by the subject as action to treat the current panic attack, anxiety episode, or PTSD flashback or to prevent onset of the future panic attack, anxiety episode, or PTSD flashback;
an audible device, wherein the activation of the audible device comprises generating an audible reminder to the subject to prompt the subject to take the action that was previously selected by the subject as action to treat the current panic attack, anxiety episode, or PTSD flashback or to prevent onset of the future panic attack, anxiety episode, or PTSD flashback; and
a display device, wherein the activation of the display device comprises outputting one or more characters on the display device to prompt the subject to take the action that was previously selected by the subject as action to treat the current panic attack, anxiety episode, or PTSD flashback or to prevent onset of the future panic attack, anxiety episode, or PTSD flashback.

12. The assembly as claimed in claim 11, wherein the device is at least one of the haptic feedback device, the audible device and the display device.

13. A method for detecting a current or future panic attack, anxiety episode, or post-traumatic stress disorder (PTSD) flashback comprising:
measuring, with at least one physiological sensor, data that indicates a change in a value of at least one physiological parameter of a subject over a time period;
measuring, with a motion sensor, data that indicates a value of a motion of the subject over the time period;
receiving, with a processor, data from the motion sensor;
determining, with the processor, whether the value of the motion of the subject over the time period is less than a motion threshold;
receiving, with the processor, data from the at least one physiological sensor if the value of the motion of the subject is less than the motion threshold;
determining, with the processor, whether the change in the value of the at least one physiological parameter over the time period exceeds a change threshold; and
performing an action based on the determination that the change in the value of the at last one physiological parameter exceeds the change threshold, comprising activating a device to alert the subject of the current or future panic attack, anxiety episode, or PTSD flashback to prompt the subject to take action to treat the current panic attack, anxiety episode, or PTSD flashback or prevent onset of the future panic attack, anxiety episode, or PTSD flashback.

14. A method as claimed in claim 13, further comprising suppressing, with the processor, data from the at least one physiological sensor if the value of the motion of the subject is greater than the motion threshold.

15. A method as claimed in claim 13, wherein the device is a haptic feedback device worn by the subject to alert the subject of the determination that the change in the value of the at last one physiological parameter exceeds the change threshold.

16. A method as claimed in claim 13, wherein the device is a display device and wherein the performing the action comprises outputting one or more characters on the display device based on the determination that the change in the value of the at least one physiological parameter exceeds the change threshold.

17. A method as claimed in claim 13, wherein the performing the action comprises providing treatment to the subject.

18. A method as claimed in claim 13, further comprising: measuring, with the at least one physiological sensor, data that indicates a resting level of the at least one physiological parameter; and determining, with the processor, at least one of the motion threshold and the change threshold based on the resting level.

19. The method as claimed in claim 13, wherein the activating the device comprises at least one of:
automatically calling or texting, with a phone, a designated phone number of the subject or a designated individual to alert the subject or the designated individual of the current or future panic attack, anxiety episode, or PTSD flashback;
generating mechanical stimulation, with a haptic feedback device, to be detected by the subject to prompt the subject to take an action that was previously selected by the subject as action to treat the current panic attack, anxiety episode, or PTSD flashback or to prevent onset of the future panic attack, anxiety episode, or PTSD flashback;

generating an audible reminder, with an audible device, to the subject to prompt the subject to take the action that was previously selected by the subject as action to treat the current panic attack, anxiety episode, or PTSD flashback or to prevent onset of the future panic attack, anxiety episode, or PTSD flashback; and outputting, on a display device, one or more characters on the display device to prompt the subject to take the action that was previously selected by the subject as action to treat the current panic attack, anxiety episode, or PTSD flashback or to prevent onset of the future panic attack, anxiety episode, or PTSD flashback.

20. The method as claimed in claim 19, wherein the action previously selected by the subject comprises at least one of:

visualizing a symbol, wherein the activating the device prompts the subject to visualize the symbol;

activating an anchor, wherein the activating the device prompts the subject to activate the anchor;

reciting a mission statement, wherein the activating the device prompts the subject to recite the mission statement; and taking a medication, wherein the activating the device prompts the subject to take the medication.

* * * * *